US012677850B2

(12) United States Patent
Bridges et al.

(10) Patent No.: US 12,677,850 B2
(45) Date of Patent: *\*Jul. 14, 2026*

(54) STEVIA BLENDS CONTAINING REBAUDIOSIDE B

(71) Applicant: Tate & Lyle Solutions USA LLC, Hoffman Estates, IL (US)

(72) Inventors: John R. Bridges, Hoffman Estates, IL (US); Alfred Carlson, Hoffman Estates, IL (US); Penelope A. Patton, Hoffman Estates, IL (US); Joshua N. Fletcher, Hoffman Estates, IL (US)

(73) Assignee: Tate & Lyle Solutions USA LLC, Hoffman Estates, IL (US)

( * ) Notice: Subject to any disclaimer, the term of this patent is extended or adjusted under 35 U.S.C. 154(b) by 173 days.

This patent is subject to a terminal disclaimer.

(21) Appl. No.: 18/372,408

(22) Filed: Sep. 25, 2023

(65) Prior Publication Data

US 2024/0091567 A1 Mar. 21, 2024

Related U.S. Application Data

(63) Continuation of application No. 16/775,949, filed on Jan. 29, 2020, now Pat. No. 11,801,402, which is a continuation of application No. 15/174,274, filed on Jun. 6, 2016, now Pat. No. 10,583,314, which is a continuation of application No. 13/276,649, filed on Oct. 19, 2011, now Pat. No. 9,402,411.

(60) Provisional application No. 61/437,390, filed on Jan. 28, 2011.

(51) Int. Cl.

| *A23L 2/60* | (2006.01) |
| *A23L 27/30* | (2016.01) |
| *A61K 8/60* | (2006.01) |
| *A61Q 11/00* | (2006.01) |

(52) U.S. Cl.
CPC ................. *A23L 2/60* (2013.01); *A23L 27/33* (2016.08); *A23L 27/36* (2016.08); *A61K 8/602* (2013.01); *A61Q 11/00* (2013.01); *A23V 2002/00* (2013.01); *A23V 2200/16* (2013.01); *A23V 2250/258* (2013.01)

(58) Field of Classification Search
CPC ................................ A23L 1/2366; A23L 2/60
USPC ............................................. 426/548; 424/49
See application file for complete search history.

(56) References Cited

U.S. PATENT DOCUMENTS

| RE30,820 E | 12/1981 | Walon |
| 4,361,697 A | 11/1982 | Dobberstein et al. |
| 4,612,942 A | 9/1986 | Dobberstein et al. |
| 5,411,755 A | 5/1995 | Downton et al. |
| 5,433,965 A | 7/1995 | Fischer et al. |
| 5,960,725 A | 10/1999 | Tseng |
| 6,335,461 B1 | 1/2002 | Amino et al. |
| 7,575,772 B2 | 8/2009 | Shi et al. |
| 7,815,956 B2 | 10/2010 | Lee et al. |
| 7,884,265 B2 | 2/2011 | Morita et al. |
| 8,017,168 B2 | 9/2011 | Prakash et al. |
| 8,962,698 B2 | 2/2015 | Bridges et al. |
| 9,024,012 B2 | 5/2015 | Erickson et al. |
| 9,044,038 B2 | 6/2015 | Yoshinaka et al. |
| 9,115,166 B2 | 8/2015 | Prakash et al. |
| 9,402,411 B2 | 8/2016 | Bridges et al. |
| 9,609,887 B2 | 4/2017 | Quinlan et al. |
| 10,583,314 B2 | 3/2020 | Bridges et al. |
| 2005/0152997 A1 | 7/2005 | Selzer et al. |
| 2006/0003053 A1 | 1/2006 | Ekanayake et al. |
| 2007/0116823 A1 | 5/2007 | Prakash et al. |
| 2007/0116825 A1 | 5/2007 | Prakash et al. |
| 2007/0116828 A1 | 5/2007 | Prakash et al. |
| 2007/0116836 A1 | 5/2007 | Prakash et al. |
| 2007/0116839 A1 | 5/2007 | Prakash et al. |
| 2007/0116840 A1 | 5/2007 | Prakash et al. |
| 2007/0224292 A1 | 9/2007 | Brunner et al. |
| 2008/0107775 A1 | 5/2008 | Prakash et al. |
| 2008/0226788 A1 | 9/2008 | Chang et al. |
| 2008/0226796 A1 | 9/2008 | Lee et al. |
| 2008/0226802 A1 | 9/2008 | Lee et al. |
| 2008/0274258 A1 | 11/2008 | Shi et al. |
| 2008/0299277 A1 | 12/2008 | Chao et al. |
| 2009/0004355 A1* | 1/2009 | Catani .................... A23L 33/20 426/548 |
| 2009/0162487 A1 | 6/2009 | Bell et al. |
| 2009/0196966 A1 | 8/2009 | West et al. |
| 2010/0099857 A1 | 4/2010 | Evans et al. |

(Continued)

FOREIGN PATENT DOCUMENTS

| CN | 1094892 A | 11/1994 |
| CN | 101062077 A | 10/2007 |

(Continued)

OTHER PUBLICATIONS

Annex to the European Search Report in European Application No. 15 17 7709, mailed Oct. 13, 2015, 1 page.

(Continued)

*Primary Examiner* — Walter E Webb

(74) *Attorney, Agent, or Firm* — Matney Legal Group PLLC

(57) ABSTRACT

The present invention relates to the use of sweet steviol glycoside compounds, particularly rebaudioside B, in sweetening compositions. Sweetening compositions comprising selected amounts of rebaudioside B have been shown to possess favorable flavor profiles when compared to other high intensity sweetener compounds and are useful in the preparation of consumables.

16 Claims, 3 Drawing Sheets

(56)                References Cited

U.S. PATENT DOCUMENTS

| | | | |
|---|---|---|---|
| 2010/0112154 A1 | 5/2010 | Abelyan et al. |
| 2010/0166679 A1 | 7/2010 | Abelyan et al. |
| 2010/0267847 A1 | 10/2010 | Yoshinaka et al. |
| 2010/0285195 A1 | 11/2010 | Fisher et al. |
| 2010/0316782 A1 | 12/2010 | Shi et al. |
| 2011/0021456 A1 | 1/2011 | Lyndon et al. |
| 2011/0023192 A1 | 1/2011 | Morita et al. |
| 2011/0038957 A1 | 2/2011 | Fowler et al. |
| 2011/0052755 A1 | 3/2011 | Fiorenza et al. |
| 2011/0160311 A1 | 6/2011 | Prakash et al. |
| 2011/0287164 A1 | 11/2011 | Markosyan |
| 2012/0059071 A1 | 3/2012 | Markosyan et al. |
| 2012/0183648 A1 | 7/2012 | Sun et al. |
| 2012/0264831 A1 | 10/2012 | Bridges et al. |
| 2012/0289687 A1 | 11/2012 | Erickson et al. |
| 2013/0071537 A1 | 3/2013 | Shi et al. |
| 2013/0136838 A1 | 5/2013 | San Miguel et al. |
| 2013/0164420 A1 | 6/2013 | Catani et al. |
| 2013/0309389 A1 | 11/2013 | Carlson et al. |
| 2014/0234511 A1 | 8/2014 | Hansen et al. |

FOREIGN PATENT DOCUMENTS

| | | |
|---|---|---|
| CN | 101327244 A | 12/2008 |
| CN | 101557726 A | 10/2009 |
| CN | 101657112 A | 2/2010 |
| CN | 101690573 A | 4/2010 |
| CN | 101854814 A | 10/2010 |
| CN | 101863946 A | 10/2010 |
| CN | 101970450 A | 2/2011 |
| CN | 102060892 A | 5/2011 |
| CN | 102084982 A | 6/2011 |
| CN | 102093445 A | 6/2011 |
| CN | 102093447 A | 6/2011 |
| CN | 103402374 A | 11/2013 |
| EP | 0154235 A2 | 9/1985 |
| EP | 2215914 A1 | 8/2010 |
| EP | 2425721 A1 | 3/2012 |
| EP | 2486806 A1 | 8/2012 |
| JP | 52083731 A | 7/1977 |
| JP | 52120170 A | 10/1977 |
| JP | 53112466 | 2/1978 |
| JP | 60199364 A | 10/1985 |
| JP | 59120073 A | 7/1994 |
| JP | 11046701 A | 2/1999 |
| JP | 2000287642 A | 10/2000 |
| JP | 2003274911 A | 9/2003 |
| JP | 2004344071 A | 12/2004 |
| JP | 2009517031 A | 3/2010 |
| JP | 2010507376 A | 3/2010 |
| JP | 2010509232 A | 3/2010 |
| JP | 2010521172 A | 6/2010 |
| JP | 2010521173 A | 6/2010 |
| JP | 2010521181 A | 6/2010 |
| JP | 2013518118 A | 12/2013 |
| JP | 2013545490 A | 12/2013 |
| JP | 6659885 B2 | 3/2020 |
| RU | 2160310 C1 | 12/2000 |
| WO | 2006072921 A2 | 7/2006 |
| WO | 2006093229 A1 | 9/2006 |
| WO | 2007061898 A1 | 5/2007 |
| WO | 2008030121 A1 | 3/2008 |
| WO | 2008057968 A1 | 5/2008 |
| WO | 2008091547 A2 | 7/2008 |
| WO | 2008112961 A1 | 9/2008 |
| WO | 2008112962 A1 | 9/2008 |
| WO | 2008112991 A2 | 9/2008 |
| WO | 2009006208 A2 | 1/2009 |
| WO | 2009016374 A1 | 2/2009 |
| WO | 2009063921 A1 | 5/2009 |
| WO | 2009071277 A1 | 6/2009 |
| WO | 2009093610 A1 | 7/2009 |
| WO | 2009086049 A2 | 9/2009 |
| WO | 2009108680 A2 | 9/2009 |
| WO | 2009140394 A1 | 11/2009 |
| WO | 2010038911 A1 | 4/2010 |
| WO | 2011066754 A1 | 6/2011 |
| WO | 2011094423 A1 | 8/2011 |
| WO | 2012068457 A1 | 5/2012 |
| WO | 2012073121 A2 | 6/2012 |
| WO | 2012082493 A1 | 6/2012 |
| WO | 2013082677 A1 | 6/2012 |
| WO | 2012088598 A1 | 7/2012 |
| WO | 2012103074 A2 | 8/2012 |
| WO | 2012108894 A1 | 8/2012 |
| WO | 2012109506 A1 | 8/2012 |
| WO | 2012109585 A1 | 8/2012 |
| WO | 2012125991 A2 | 9/2012 |
| WO | 2012166163 A1 | 12/2012 |
| WO | 2012166164 A1 | 12/2012 |
| WO | 2012177727 A1 | 12/2012 |
| WO | 2013036366 A1 | 3/2013 |
| WO | 2013036768 A1 | 3/2013 |

OTHER PUBLICATIONS

Australian Examination Report for Australian Application No. 2012209241, dated Mar. 17, 2015, 5 pages.
Australian Examination Report for Australian Application No. 2013296597, dated Feb. 2, 2016, 3 pages.
Chinese Notice of Decision of Rejection for Chinese Application No. 201180069627.7, dated Dec. 2, 2015, 11 pages.
Chinese Office Action for Chinese Application No. 201180069627. 7, dated Jul. 1, 2014, 17 pages.
Chinese Office Action for Chinese Application No. 201180069627. 7, dated May 21, 2015, 10 pages.
Chinese Office Action for Chinese Application No. 201280010780. 7, dated Dec. 24, 2014, 13 pages.
Chinese Office Action for Chinese Application No. 201380040911. 0, dated Jan. 4, 2016, 13 pages.
Compounds (C26H30O10) provided by Chemspider (http://www. chemspider.com/Search.aspx?rid=5a954e4d-41f8-b7do-1be5cea4bba), downloaded on Apr. 2, 2013, 10 pages.
Provisional Application for Stevia Blends Containing Rebaudioside B, filed Jan. 28, 2011, 43 pages.
Crammer et al., "Progress in the Chemistry and Properties of Rebaudiosides", Development in Sweeteners-3, Elsevier Applied Science, London Polypeptide, 1987, pp. 45-64.
Definition of Consumable from Websters Online Dictionary, uploaded May 27, 2016, 1 page.
First Notice of Opposition for European Patent No. 2667732, dated Apr. 29, 2016, 20 pages.
Final Office Action for U.S. Appl. No. 13/276,649, mailed Apr. 8, 2014, 8 pages.
Final Office Action for U.S. Appl. No. 13/276,649, mailed Jul. 22, 2015, 10 pages.
Final Office Action for U.S. Appl. No. 13/956,996, mailed Sep. 19, 2016, 17 pages.
Gelski, J., "Sweetener Combines Stevia, Luo Han Guo Fruit", FoodBusinessNews.net, Jun. 13, 2011, 1 page.
International Search Report and Written Opinion issued for International Application No. PCT/US2012/022339, mailed Sep. 27, 2012, 6 pages.
International Search Report and Written Opinion issued for International Application No. PCT/US2013/052821, mailed Oct. 30, 2013, 10 pages.
Japanese Decision of Final Rejection for Japanese Application No. 2013-551961, mailed Dec. 1, 2015, 6 pages.
Japanese Informative Statement for Japanese Application No. 2013-551285, mailed Jan. 30, 2015, 5 pages.
Japanese Notice of Reasons for Rejection for Japanese Application No. 2015-525529, dated May 26, 2017, with translation, 5 pages.
Japanese Notice of Reasons for Rejection for Japanese Application No. 2015-525529, dated Jan. 30, 2018, with translation, 5 pages.
Japanese Notice of Reasons for Rejection for Japanese Application No. 2015-525529, dated May 12, 2020 with translation, 4 pages.
Japanese Office Action for Japanese Application No. 2016-074144, dated Nov. 7, 2017, 5 pages.

(56) References Cited

OTHER PUBLICATIONS

Kasai et al., "Synthesis of Sweet Diterpene-Glycoside of Leaves of Stevia; rebaudiosides-A, -D, -E and their relating glycosides as well as Relationship between their Sweetness and Chemical Structure", Journal of Chemical Society, Japan 1981 (5), pp. 726-735 with translation.

Kinghorn, D., "Stevia, The Genus Stevia", chapter 1, published 2002, 22 pages.

Kinghorn, D., Studies to Identify, Isolate, Develop and Test Naturally Occurring Noncariogenic Sweeteners that May be Used as Dietary Sucrose Substitutes, Comprehensive Technical Report for the Period Jun. 25, 1980-Sep. 24, 1983, 35 pages.

Kohda et al., "New Sweet Diterpene Glucosides from Stevia Rebaudiana", Phytochemistry, 1976, vol. 14, pp. 981-983.

"Layn's Luo Han Guo Natural Sweetener has achieved GRAS status", Lovia Taking Stevia to the Next Level, Layn Natural Ingredients, http://www.layncorp.com/news.php (May 1, 2011), 1 page.

"Lovia", Layn Natural Ingredients, http://www.layncorp.com/showproducts.php?id+126, accessed on Jan. 20, 2012, 2 ogs.

Mizukami et al., "Enzymatic Determination of Stevioside in Stevia Rebaudiana", Phytochemistry, 1982, vol. 21, No. 8, pp. 1927-1930.

Mosciano, G., "Developing a Common Language Between Flavorists and Product Developers", Perfumer & Flavorist, vol. 25, (Mar./Apr. 2000), 6 pages.

Non Final Office Action for U.S. Appl. No. 13/276,649, mailed Jul. 28, 2014, 8 pages.

Non Final Office Action for U.S. Appl. No. 13/276,649, mailed Jun. 10, 2015, 20 pages.

Non Final Office Action for U.S. Appl. No. 13/276,649, mailed Jun. 17, 2016, 12 pages.

Notice of Allowance for U.S. Appl. No. 13/276,649, mailed May 19, 2016, 24 pages.

Notice of Opposition to European Patent No. 2954786, Application No. 15177709.1, dated Jan. 2, 2019, 30 pages.

Notification of International Preliminary Report on Patentability and Written Opinion issued for PCT/US2012/022339 on Jul. 30, 2013, 20 pages.

Office Action for U.S. Appl. No. 13/956,996, mailed Aug. 31, 2015, 29 pages.

Office Action for U.S. Appl. No. 13/956,996, mailed Mar. 3, 2015, 29 pages.

Ohtani et al., "Methods to improve the taste of the sweet principles of Stevia rebaudiana", Stevia. The Genus Stevia., CRC Press 2001, pp. 138-159.

Partial International Search Report for PCT/US2012/022339, dated Jun. 22, 2012, 2 pages.

Schiffman et al., "Investigation of Synergism in Binary Mixtures of Sweeteners", Brain Research Bulletin, vol. 38, No. 2 (Jan. 20, 1995), pp. 105-120.

Schiffman et al., "Synergism among Ternary Mixtures of Fourteen Sweeteners", Chem. Senses 25, (2000), pp. 131-140.

Second Notice of Opposition for European Patent for European Application No. 2667732, dated Apr. 29, 2016, 26 pages.

Sharma et al., "Chemistry and in vivo profile of ent-kaurene glycosides of Stevia rebaudiana Bertoni—An Overview", Natural Product Radiance, vol. 8(2), 2009, pp. 181-189.

Tanaka, O., "Improvement of taste of natural sweeteners", Pure & Appl. Che., vol. 69, No. 4, 1997, pp. 675-683.

Translation of Japanese Office Action for Japanese Application No. 2013-551961, mailed May 12, 2015, 5 pages.

UKIPO Combined Search and Examination Report issued for Application No. GB1217700.2, dated Jan. 29, 2013 6 pages.

Wolwer-Rieck et al., "Investigations on the stability of stevioside and rebaudioside a in soft drinks", J. Agric. Food Chem, 58(23),Dec. 8, 2010, p. 12216-12220.

Yuqiang et al., "Production of B-fructofuranosidase and Optimization of Enzymatic Modification Process for Stevioside and Rebaudioside A," Food and Fermentation, vol. 35, Issue 3, pp. 23-27, Dec. 21, 2009: Abstract Only.

Entire patent prosecution history of U.S. Appl. No. 13/276,649, filed Oct. 19, 2011, now U.S. Pat. No. 9,402,411, issued Aug. 2, 2016, entitled, "Stevia Blends Containing Rebaudioside B".

Entire patent prosecution history of U.S. Appl. No. 15/174,274, filed Jun. 6, 2016, entitled, "Stevia Blends Containing Rebaudioside B."

Entire patent prosecution history of U.S. Appl. No. 16/775,949, filed Jan. 29, 2020, entitled, "Stevia Blends Containing Rebaudioside B."

Kinghorn, D., "Stevia, The Genus Stevia", chapters 4 and 9, 38 pages. Published 2002.

* cited by examiner

The solubility of Reb B, as a function of Reb A and Steviocide concentrations, in pH 3 citric acid/citrate buffer

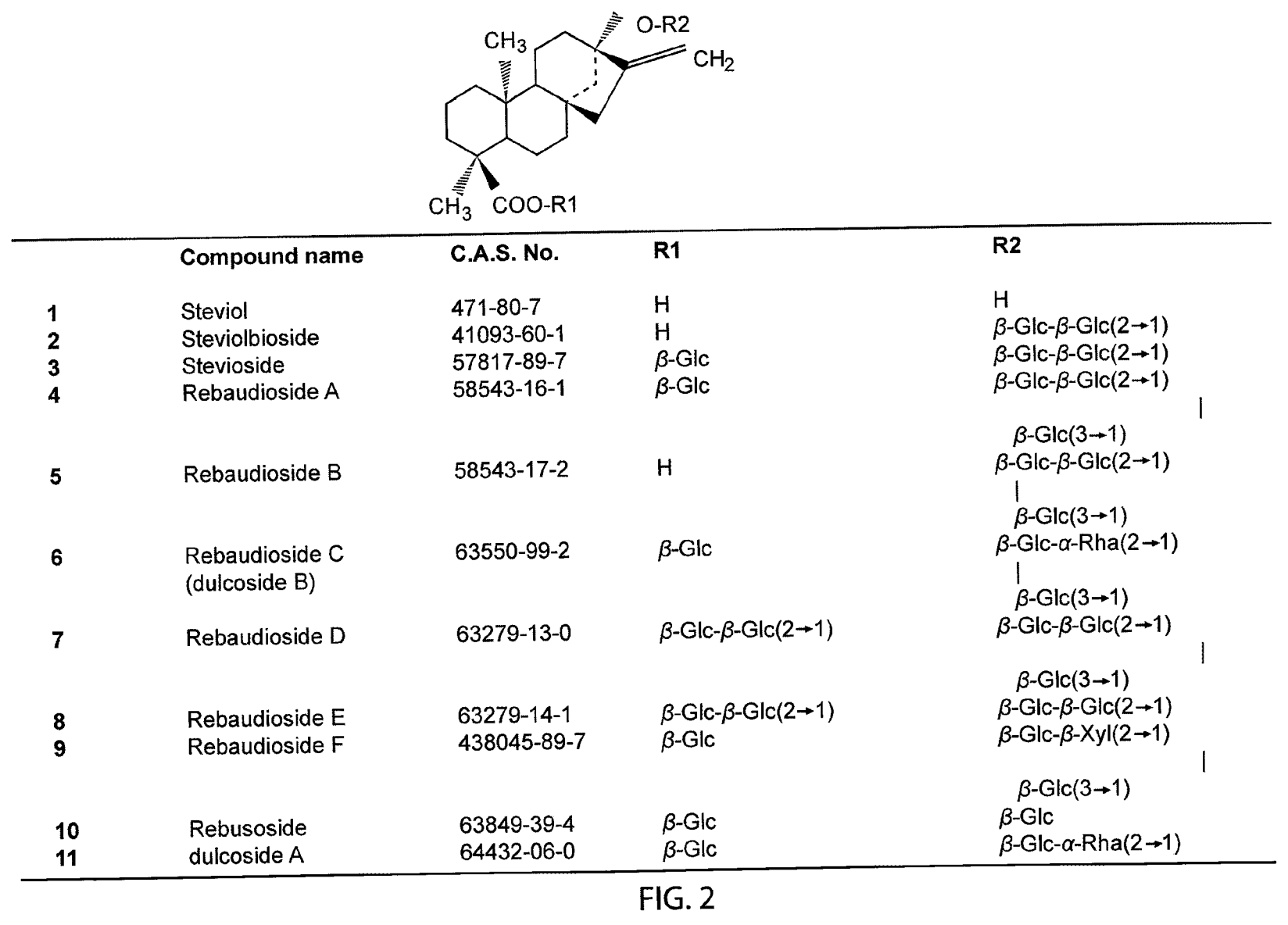

| | Compound name | C.A.S. No. | R1 | R2 |
|---|---|---|---|---|
| 1 | Steviol | 471-80-7 | H | H |
| 2 | Steviolbioside | 41093-60-1 | H | β-Glc-β-β-Glc(2→1) |
| 3 | Stevioside | 57817-89-7 | β-Glc | β-Glc-β-β-Glc(2→1) |
| 4 | Rebaudioside A | 58543-16-1 | β-Glc | β-Glc-β-β-Glc(2→1) |
| 5 | Rebaudioside B | 58543-17-2 | H | β-Glc(3→1)<br>β-Glc-β-Glc(2→1) |
| 6 | Rebaudioside C (dulcoside B) | 63550-99-2 | β-Glc | β-Glc(3→1)<br>β-Glc-α-Rha(2→1) |
| 7 | Rebaudioside D | 63279-13-0 | β-Glc-β-Glc(2→1) | β-Glc(3→1)<br>β-Glc-β-Glc(2→1) |
| 8 | Rebaudioside E | 63279-14-1 | β-Glc-β-Glc(2→1) | β-Glc(3→1)<br>β-Glc-β-Glc(2→1) |
| 9 | Rebaudioside F | 438045-89-7 | β-Glc | β-Glc-β-Xyl(2→1) |
| 10 | Rebusoside | 63849-39-4 | β-Glc | β-Glc(3→1)<br>β-Glc |
| 11 | dulcoside A | 64432-06-0 | β-Glc | β-Glc-α-Rha(2→1) |

FIG. 2

STEVIA BLENDS CONTAINING REBAUDIOSIDE B

CROSS-REFERENCE TO RELATED APPLICATIONS

This application is a Continuation of U.S. application Ser. No. 16/775,949 filed on Jan. 29, 2020, which is a Continuation of U.S. application Ser. No. 15/174,274, filed on Jun. 6, 2016, now U.S. Pat. No. 10,583,314 issued on Mar. 10, 2020, which is a Continuation of U.S. application Ser. No. 13/276,649, filed on Oct. 19, 2011, now U.S. Pat. No. 9,402,411, issued on Aug. 2, 2016, which claims the benefit of U.S. Provisional Patent Application No. 61/437,390, filed Jan. 28, 2011. The disclosure of each of these applications is incorporated herein by reference in its entirety for all purposes.

STATEMENT REGARDING FEDERALLY SPONSORED RESEARCH OR DEVELOPMENT

Not Applicable.

BACKGROUND

Natural caloric sweeteners, such as sucrose, glucose, and fructose, possess desirable taste characteristics, but they add to the caloric content of products. Therefore, there is great consumer interest in low or non-caloric sweeteners that are considered as healthier alternatives. Non-caloric natural and synthetic high-potency sweeteners are known, but they most often possess flavor profiles that are not as desirable to consumers as sugars. Thus, it is desirable to develop non-caloric sweeteners that can be substituted for sugar and that have a more desirable taste profile.

The species *Stevia rebaudiana* ("*Stevia*") is the source of certain naturally occurring sweet steviol glycosides. Considerable research and development has been done to evaluate the use of sweet steviol glycosides of *Stevia* as non-caloric sweeteners, Sweet steviol glycosides that may be extracted from *Stevia* include the six rebaudiosides (i.e., rebaudioside A to F), stevioside (the predominant glycoside in extracts from wild type *Stevia*), and dulcosides.

Commercial low or non-caloric sweeteners based on rebaudioside A and other steviol glycosides tend to have bitter and licorice aftertastes. These characteristics are especially notable at concentrations above about 300 ppm. In food applications, preferred use levels (8-10% sugar equivalence values) are typically about 500 ppm to about 1000 ppm, above the range at which off tastes are first noticed. Thus a need continues to exist for reduced-, low-, and/or non-caloric sweeteners comprising sweet steviol glycosides that have taste profiles with reduced or no bitterness, undesirable flavors (e.g., licorice), or sweetness profiles more like natural caloric sweeteners, or combinations of such properties.

SUMMARY OF THE INVENTION

The present invention is directed to a *Stevia* extract comprising rebaudioside B at a concentration that is in the range of 10 to about 90% by weight of the *Stevia* extract.

The present invention is also directed to a sweetening composition comprising sweet steviol glycoside compounds, wherein the sweet steviol glycoside compounds comprise rebaudioside B at a concentration that is in the range of 10% to about 90% by weight of the total amount of sweet steviol glycoside compounds in the sweetening composition.

The present invention is also directed to consumables such as beverages, foodstuffs, oral care products, tobacco products, pharmaceutical products, and nutraceutical products comprising the foregoing sweetening compositions and methods of the sweetening the same using the foregoing sweetening compositions.

BRIEF DESCRIPTION OF THE DRAWINGS

FIG. 2 shows the structures of steviol glycosides.

DETAILED DESCRIPTION

I. Definitions

Figure 1:
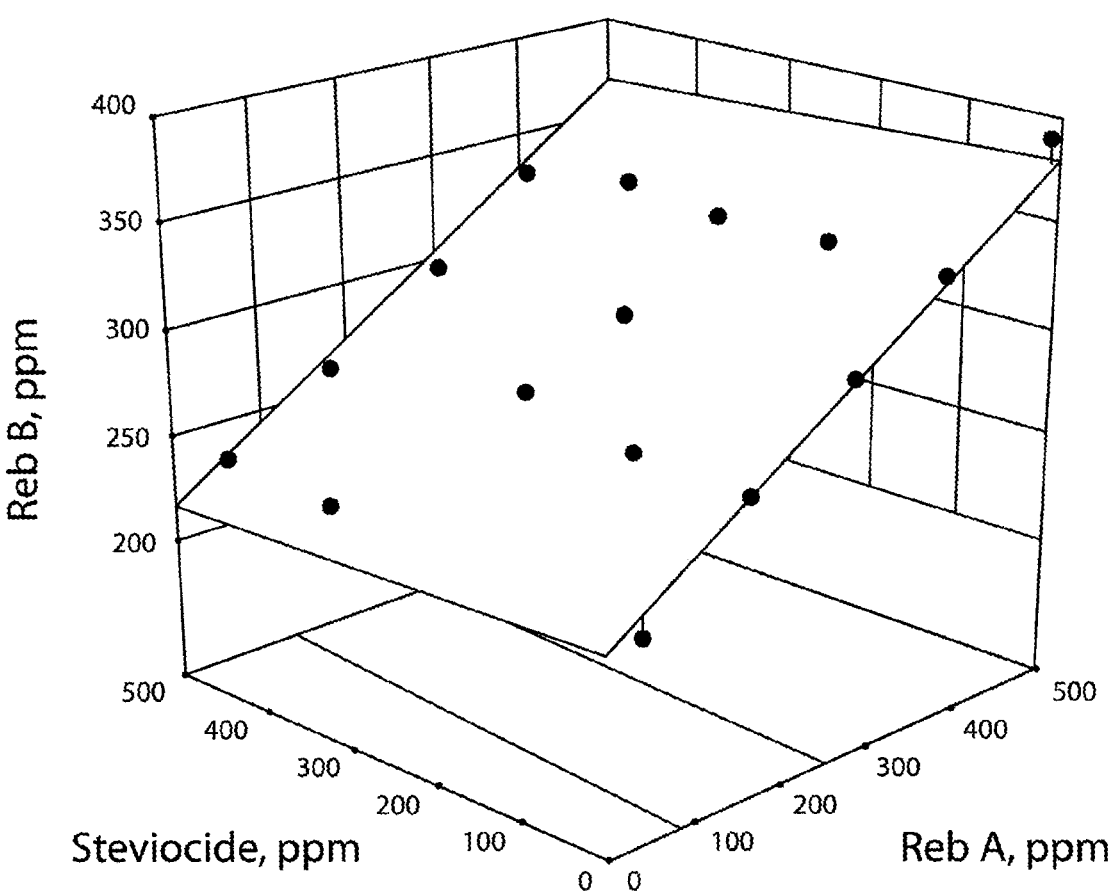
FIG. 1 is a graph showing the solubility of rebaudioside B in citric acid buffer at pH of 3 as a function of rebaudioside A and stevioside concentrations.

As used herein, the phrase "sweet steviol glycoside compounds" means any of a number of naturally occurring compounds with a general structure of the steviol diterpene ring system with one or more saccharide residues chemically attached to the ring.

II. Overview

It has unexpectedly been discovered that by including and/or controlling the concentration of rebaudioside B in *Stevia* extracts and sweetening compositions comprising sweet steviol glycosides tends to reduce or eliminate taste characteristics generally considered to be negative such as bitterness, licorice aftertaste, or result in a sweetness profile more like that of natural caloric sweeteners, or combinations of such properties. Specifically, it has been discovered that the foregoing benefits may be achieved by selecting a relatively high concentration of rebaudioside B with respect to the total concentration of sweet steviol glycosides in the *Stevia* extract and sweetening composition (e.g., at least 10% by weight of the total amount of sweet steviol glycoside compounds being rebaudioside B).

The aforementioned *Stevia* extracts and sweetening compositions of the present invention are useful as reduced-caloric, low-caloric, or non-caloric sweeteners in foodstuffs, i.e., edible or chewable compositions such as food, beverages, medicine, candy, chewing gum, and the like. It has been discovered that the *Stevia* extract and sweetening compositions of the present invention can possess a sweetness profile that is more sugar-like, reduced bitter aftertaste, reduced off flavors (e.g., licorice) than other mixtures of sweet steviol glycosides, such as commercially available blends and mixtures of steviol glycosides. Testing has shown that, in most cases, sweetening compositions of the present invention are preferred by test subjects over compositions that comprise 97% rebaudioside A, when tested at the same concentration. Adding *Stevia* extract and sweetening compositions of the present invention to foods and beverages is expected to result in better tasting foods and beverages compared to those prepared with known *Stevia* extracts and sweetening compositions containing sweet steviol glycosides, such as compositions having 97% rebaudioside A.

It is also contemplated that rebaudioside B may be added to other high intensity sweeteners. Representative examples of high intensity sweeteners suitable for embodiments of the invention include natural high intensity sweeteners such as:

dulcoside A, dulcoside B (also known as rebaudioside C), rubusoside, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, stevioside, rebaudioside A, rebaudioside D, rebaudioside E, rebaudioside F, *Stevia*, steviolmonosides, and steviolbiosides;

and artificial high intensity sweeteners such as:

saccharin, aspartame, sucralose, neotame, acesulfame potassium.

Further, one of skill in the art will recognize that rebaudioside B can be added to caloric sweeteners, such as sugars (e.g., high fructose corn syrup, sucrose, fructose, etc.) and polyols (e.g., sorbitol, xylitol, lactitol, etc.) or other low-calorie sweeteners to produce sweetening compositions that are reduced in caloric value.

Simple extraction of steviol glycosides from plants generally results in extracts that are less preferred in terms of taste than purified extracts higher in rebaudioside A. However, simple extracts are easier to produce and are generally less expensive to produce than high purity rebaudioside A. Therefore, a further advantage of the present invention may be a combination of a simple extract or partially purified product with rebaudioside B, so as to obtain a glycoside mixture that is less expensive to produce than purified rebaudioside A, yet possesses comparable or superior flavor characteristics. It is also contemplated that steviol glycoside processing streams that have been depleted of good tasting glycosides during the purification of rebaudioside A can be made to taste better by increasing the rebaudioside B content.

The compositions containing rebaudioside B may be further modified using known technology to modify particle size such as agglomeration, spray-drying, drum drying and other forms of physical processing commonly applied to adjust particle size in order to deliver better flow, hydration, or dissolution properties.

The compositions containing rebaudioside B may be further modified using known technology to provide liquid forms with preservative for ease-of-use in specific applications.

The compositions containing rebaudioside B may be further modified using known techniques to co-process with bulking agents such as maltodextrins and similar compounds to deliver products with controlled sweetness, dosing, potency, and handling properties. Further, it is to be noted that rebaudioside B and/or combinations of it and other steviol glycosides can be combined with other ingredients that may be desirable to include in a sweetening composition. For example, rebaudioside B may be spray coated or spray agglomerated onto rebaudioside A or other steviol glycosides and/or with other materials such as maltodextrins, sucrose, or any other desired functional carrier.

III. *Stevia* Extracts and Sweetening Compositions Comprising Rebaudioside B It has been discovered that the taste of sweet steviol glycoside mixtures and blends (e.g., steviol glycoside mixtures and blends) can be improved by controlling and/or increasing the concentrations of rebaudioside B in steviol glycoside compositions in accordance with the present invention. It is believed that the improved taste is evident at pH values from about pH 2 to about pH 8.

The solubility limits of rebaudioside B were determined (see Example 5). For example, experimental results to date indicate that (i) rebaudioside B has relatively high solubility in neutral pH solution and (ii) the solubility of rebaudioside B is limited in a pH 3 citric buffer. Further experimental results to date indicate that the presence of rebaudioside A in solution increases the solubility of rebaudioside B. On the other hand, experimental results to date indicate that the presence of stevioside slightly reduces the solubility of rebaudioside B. This solubility information may be considered when formulating solutions of rebaudioside B and mixtures of rebaudiosides.

Rebaudioside B for mixing with other sweeteners can be obtained in various ways. For example, rebaudioside B can be isolated from plant extracts by chromatography, precipitation, or crystallization. Alternatively, rebaudioside B may be obtained by treating rebaudioside A with various hydroxides of mono, di, and trivalent cations under appropriate temperature and pH conditions. The rebaudioside B mixture with residual rebaudioside A can be used to increase the amount of rebaudioside B in another mixture, or the rebaudioside B can be isolated from the rebaudioside A/rebaudioside B mixture by chromatography, precipitation, or selective crystallization. Rebaudioside B can also be obtained in a similar manner by treating rebaudioside D with the same hydroxide compounds as mentioned above for rebaudioside A. The product mixture or isolated rebaudioside B can be used to prepare the above mentioned improved tasting steviol glycoside mixtures. As another alternative, rebaudioside B can be produced enzymatically from rebaudioside A or rebaudioside D.

In certain embodiments, a *Stevia* extract or sweetening composition comprises rebaudioside B and one or more additional sweet glycoside compounds. Representative examples of sweet glycoside compounds include rebaudioside A, rebaudioside B, rebaudioside C (dulcoside B), rebaudioside D, rebaudioside E, rebaudioside F, *Stevia*, stevioside, dulcoside A, and rubusoside. In certain embodiments, the one or more sweet glycosides may be sweet steviol glycosides, including steviolbiosides and steviolmonosides. More specifically, representative examples of sweet steviol glycosides include rebaudioside A, rebaudioside B, rebaudioside C, rebaudioside D, rebaudioside E, rebaudioside F, and stevioside. For example, partially purified extractions of steviol glycosides from plants often comprise a mixture of rebaudioside B and additional steviol glycosides.

In certain embodiments where a *Stevia* extract or sweetening composition comprises rebaudioside B and one or more additional sweet steviol glycoside compounds, the amount of rebaudioside B is at a concentration that is at least about 10% by weight of the total amount of sweet steviol glycoside compounds in the *Stevia* extract or sweetening composition. In certain embodiments the rebaudioside B is at a concentration that is at least about 15% by weight of the total amount of sweet steviol glycoside compounds in the *Stevia* extract or sweetening composition. In certain embodiments the rebaudioside B is at a concentration that is at least about 20% by weight of the total amount of sweet steviol glycoside compounds in the *Stevia* extract or sweetening composition. In certain embodiments the rebaudioside B is at a concentration that is at least about 25% by weight of the total amount of sweet steviol glycoside compounds in the

*Stevia* extract or sweetening composition. In certain embodiments the rebaudioside B is at a concentration that is at least about 30% by weight of the total amount of sweet steviol glycoside compounds in the *Stevia* extract or sweetening composition. In certain embodiments the rebaudioside B is at a concentration that is at least about 35% by weight of the total amount of sweet steviol glycoside compounds in the *Stevia* extract or sweetening composition. In certain embodiments the rebaudioside B is at a concentration that is at least about 40% by weight of the total amount of sweet steviol glycoside compounds in the *Stevia* extract or sweetening composition. In certain embodiments the rebaudioside B is at a concentration that is at least about 45% by weight of the total amount of sweet steviol glycoside compounds in the *Stevia* extract or sweetening composition. In certain embodiments the rebaudioside B is at a concentration that is at least about 50% by weight of the total amount of sweet steviol glycoside compounds in the *Stevia* extract or sweetening composition.

In certain embodiments where a *Stevia* extract or sweetening composition comprises rebaudioside B and one or more additional sweet steviol glycoside compounds and where the concentration of rebaudioside B is at a concentration consistent with any of the embodiments described above (the term "consistent" rules out potential combinations wherein a lower limit of a range from above is selected that is greater than an upper limit of a range from below), the concentration of rebaudioside B may also be at a concentration that is not greater than about 90% by weight of the total amount of sweet steviol glycoside compounds in the *Stevia* extract or sweetening composition. In certain embodiments where the concentration of rebaudioside B is at a concentration consistent with any of the embodiments described above, the concentration of rebaudioside B is not greater than about 80% by weight of the total amount of sweet steviol glycoside compounds in the *Stevia* extract or sweetening composition. In certain embodiments where the concentration of rebaudioside B is at a concentration consistent with any of the embodiments described above, the concentration of rebaudioside B is not greater than about 70% by weight of the total amount of sweet steviol glycoside compounds in the *Stevia* extract or sweetening composition. In certain embodiments where the concentration of rebaudioside B is at a concentration consistent with any of the embodiments described above, the concentration of rebaudioside B is not greater than about 60% by weight of the total amount of sweet steviol glycoside compounds in the *Stevia* extract or sweetening composition. In certain embodiments where the concentration of rebaudioside B is at a concentration consistent with any of the embodiments described above, the concentration of rebaudioside B is not greater than about 50% by weight of the total amount of sweet steviol glycoside compounds in the *Stevia* extract or sweetening composition. In certain embodiments where the concentration of rebaudioside B is at a concentration consistent with any of the embodiments described above, the concentration of rebaudioside B is not greater than about 40% by weight of the total amount of sweet steviol glycoside compounds in the *Stevia* extract or sweetening composition. In certain embodiments where the concentration of rebaudioside B is at a concentration consistent with any of the embodiments described above, the concentration of rebaudioside B is not greater than about 35% by weight of the total amount of sweet steviol glycoside compounds in the *Stevia* extract or sweetening composition. In certain embodiments where the concentration of rebaudioside B is at a concentration consistent with any of the embodiments described above, the concentration of rebaudioside B is not greater than about 30% by weight of the total amount of sweet steviol glycoside compounds in the *Stevia* extract or sweetening composition. In certain embodiments where the concentration of rebaudioside B is at a concentration consistent with any of the embodiments described above, the concentration of rebaudioside B is not greater than about 25% by weight of the total amount of sweet steviol glycoside compounds in the *Stevia* extract or sweetening composition.

In certain embodiments, the one or more additional sweet steviol glycoside compound comprises rebaudioside A. For example, partially purified extractions of steviol glycosides may comprise a mixture of rebaudioside B and rebaudioside A or rebaudioside B may be incorporated into purified preparations of rebaudioside A. In certain embodiments comprising rebaudioside A, the amount of rebaudioside A in the *Stevia* extract or sweetening composition is at a concentration that is at least about 1% by weight of the total amount of sweet steviol glycoside compounds in the *Stevia* extract or sweetening composition. In certain embodiments the amount of rebaudioside A is at least about 5% by weight of the total amount of sweet steviol glycoside compounds in the *Stevia* extract or sweetening composition. In certain embodiments the amount of rebaudioside A is at least about 10% by weight of the total amount of sweet steviol glycoside compounds in the *Stevia* extract or sweetening composition. In certain embodiments the amount of rebaudioside A is at least about 20% by weight of the total amount of sweet steviol glycoside compounds in the *Stevia* extract or sweetening composition. In certain embodiments the amount of rebaudioside A is at least about 30% by weight of the total amount of sweet steviol glycoside compounds in the *Stevia* extract or sweetening composition. In certain embodiments the amount of rebaudioside A is at least about 40% by weight of the total amount of sweet steviol glycoside compounds in the *Stevia* extract or sweetening composition. In certain embodiments the amount of rebaudioside A is at least about 50% by weight of the total amount of sweet steviol glycoside compounds in the *Stevia* extract or sweetening composition. In certain embodiments the amount of rebaudioside A is at least about 60% by weight of the total amount of sweet steviol glycoside compounds in the *Stevia* extract or sweetening composition. In certain embodiments the amount of rebaudioside A is at least about 70% by weight of the total amount of sweet steviol glycoside compounds in the *Stevia* extract or sweetening composition.

In certain embodiments comprising rebaudioside A wherein the concentration of rebaudioside A is at a concentration consistent with any of the embodiments described above, the rebaudioside A is at a concentration that is not greater than about 95% by weight of the total amount of sweet steviol glycoside compounds in the *Stevia* extract or sweetening composition. In certain embodiments comprising rebaudioside A where the concentration of rebaudioside A is at a concentration consistent with any of the embodiments described above, the rebaudioside A is at a concentration that is not greater than about 90% by weight of the total amount of sweet steviol glycoside compounds in the *Stevia* extract or sweetening composition. In certain embodiments comprising rebaudioside A where the concentration of rebaudioside A is at a concentration consistent with any of the embodiments described above, the rebaudioside A is at a concentration that is not greater than about 85% by weight of the total amount of sweet steviol glycoside compounds in the *Stevia* extract or sweetening composition. In certain embodiments comprising rebaudioside A where the concentration of rebaudioside A is at a concentration consistent with any of the embodiments described above, the rebaudioside A is at a concentration that is not greater than about 80% by weight of the total amount of sweet steviol glycoside compounds in the *Stevia* extract or sweetening composition. In certain embodiments comprising rebaudioside A where the concentration of rebaudioside A is at a concentration consistent with any of the embodiments described above, the rebaudioside A is at a concentration that is not greater than about 75% by weight of the total amount of sweet steviol glycoside compounds in the *Stevia* extract or sweetening composition. In certain embodiments comprising rebaudioside A where the concentration of rebaudioside A is at a concentration consistent with any of the embodiments described above, the rebaudioside A is at a concentration that is not greater than about 70% by weight of the total amount of sweet steviol glycoside compounds in the *Stevia* extract or sweetening composition. In certain embodiments comprising rebaudioside A where the concentration of rebaudioside A is at a concentration consistent with any of the embodiments described above, the rebaudioside A is at a concentration that is not greater than about 65% by weight of the total amount of sweet steviol glycoside compounds in the *Stevia* extract or sweetening composition. In certain embodiments comprising rebaudioside A where the concentration of rebaudioside A is at a concentration consistent with any of the embodiments described above, the rebaudioside A is at a concentration that is not greater than about 60% by weight of the total amount of sweet steviol glycoside compounds in the *Stevia* extract or sweetening composition. In certain embodiments comprising rebaudioside A where the concentration of rebaudioside A is at a concentration consistent with any of the embodiments described above, the rebaudioside A is at a concentration that is not greater than about 55% by weight of the total amount of sweet steviol glycoside compounds in the *Stevia* extract or sweetening composition. In certain embodiments comprising rebaudioside A where the concentration of rebaudioside A is at a concentration consistent with any of the embodiments described above, the rebaudioside A is at a concentration that is not greater than about 50% by weight of the total amount of sweet steviol glycoside compounds in the *Stevia* extract or sweetening composition.

Although sweetening compositions of the invention may comprise mixtures of various types of sweeteners in various quantities, in certain embodiments, a sweetening composition with rebaudioside B and one or more additional sweet steviol glycoside compounds consists essentially of sweet steviol glycoside compounds. For example, in such embodiments the total concentration of rebaudioside B and all other sweet steviol glycoside compounds present therein provide essentially all the sweetness functionality of the sweetening composition. The amount of other sweetening compounds that could be included in sweetening compositions that consists essentially rebaudioside and sweet steviol glycoside compounds will depend upon the type of other sweetening compound in question and its sweetness threshold concentration below which it is believed it does not appreciably contribute to the sweetness of a sweetening composition. Further, in certain embodiments, a sweetening composition with rebaudioside B and one or more additional sweet steviol glycoside compounds consists of sweet steviol glycoside compounds.

In certain embodiments the *Stevia* extract or sweetening composition comprising rebaudioside B and one or more additional sweet steviol glycoside compounds comprises stevioside. In certain embodiments, the concentration of stevioside is at least about 1% by weight of the total amount of sweet steviol glycoside compounds in the *Stevia* extract or sweetening composition. In certain embodiments, the concentration of stevioside is at least about 5% by weight of the total amount of sweet steviol glycoside compounds in the *Stevia* extract or sweetening composition. In certain embodiments, the concentration of stevioside is at least about 10% by weight of the total amount of sweet steviol glycoside compounds in the *Stevia* extract or sweetening composition. In certain embodiments, the concentration of stevioside is at least about 20% by weight of the total amount of sweet steviol glycoside compounds in the *Stevia* extract or sweetening composition. In certain embodiments, the concentration of stevioside is at least about 30% by weight of the total amount of sweet steviol glycoside compounds in the *Stevia* extract or sweetening composition. In certain embodiments, the concentration of stevioside is at least about 40% by weight, of the total amount of sweet steviol glycoside compounds in the *Stevia* extract or sweetening composition. In certain embodiments, the concentration of stevioside is not greater than about 95% by weight of the total amount of sweet steviol glycoside compounds in the *Stevia* extract or sweetening composition. In certain embodiments, the concentration of stevioside is not greater than about 90% by weight of the total amount of sweet steviol glycoside compounds in the *Stevia* extract or sweetening composition. In certain embodiments, the concentration of stevioside is not greater than about 80% by weight of the total amount of sweet steviol glycoside compounds in the *Stevia* extract or sweetening composition. In certain embodiments, the concentration of stevioside is not greater than about 70% by weight of the total amount of sweet steviol glycoside compounds in the *Stevia* extract or sweetening composition. In certain embodiments, the concentration of stevioside is not greater than about 60% by weight of the total amount of sweet steviol glycoside compounds in the *Stevia* extract or sweetening composition.

IV. Products Comprising High Rebaudioside B Sweeteners

Certain embodiments of the invention are drawn to foodstuffs comprising *Stevia* extract or sweetening compositions with high concentrations of rebaudioside B. One of skill in the art would recognize any edible or chewable composition may be sweetened in accordance with the present inventions, such as foodstuffs, (e.g., snacks, baked goods, soups, sauces, processed meats canned fruits, canned vegetables, dairy products, frozen confections, cakes, cookies, bars, and other sweet bakery items, cereals, cereal bars, yogurt, yogurt-containing drinks, energy bars, granola bars, hard candy, jelly candy, chocolate candy, and other sweet confections); beverages (e.g., carbonated soft drinks, ready to drink teas, sports drinks, dairy drinks, alcoholic beverages, energy drinks, coffees, flavored waters, vitamin drinks, fruit drinks, and fruit juices, powdered soft drinks), medicines or pharmaceutical products (e.g., tablets, lozenges, suspensions, etc. nutraceutical products (e.g., supplements, vitamins, etc.), candy or confections; chewing gum; tobacco products (e.g., chewing tobacco); and the like. The addition of rebaudioside B or *Stevia* extracts or sweetening compositions comprising rebaudioside B and other optional sweeteners to foodstuffs is a process that will depend on the foodstuff and its preparation. Such preparation is known to those skilled in the art of preparing foodstuffs. Preferably, the sweetening composition is included in an effective amount that imparts the desired amount of sweetness to foodstuff. One of skill in the art would recognize that it is routine practice to determine the preferred amount of sweetener to add in the preparation of foodstuffs.

In certain embodiments, the foodstuff contains a sweetening composition comprising rebaudioside B and one or more additional sweet steviol glycoside compounds as described herein. In certain embodiments, steviol glycosides of the sweetening composition are at a total concentration that is less than their sweetening threshold (which is believed to be about 40 ppm). In such an embodiment, it is believed that at such low amounts the sweet steviol glycosides are functioning as a flavoring agent or a flavor enhancing agent rather than as a sweetener. In certain embodiments, the sweet steviol glycosides of the sweetening composition are at a total concentration that is at least about 50 ppm. In certain embodiments, the sweet steviol glycosides of the sweetening composition are at a total concentration that is at least about 200 ppm, or at a concentration that is at least about 500 ppm, or at a concentration that is at least about 1500 ppm.

In certain embodiments, the foodstuff is a beverage containing a sweetening composition comprising rebaudioside B and one or more additional sweet steviol glycoside compounds as described herein. In certain embodiments, the pH of the beverage is at least about pH 2 (and preferably at least about pH 4) and not greater than about pH 8. In certain embodiments, the sweet steviol glycosides of the sweetening composition are at a total concentration that is at least about 50 ppm. In certain embodiments, the sweet steviol glycosides of the sweetening composition are at a total concentration that is at least about 200 ppm, or at least about 500 ppm, or at least about 1500 ppm.

V. Production of Sweetening Composition

Sweetening compositions in accordance with the principles set forth herein may be produced according to any appropriate method of which there are a variety. One such method involves blending certain amounts of rebaudioside B with and one or more additional sweet steviol glycoside compounds such as rebaudioside A and/or other sweet steviol glycoside compounds. For example a blend of purified rebaudioside B and rebaudioside A and/or other sweet steviol glycoside compounds may be made by blending dry powders of the components. Alternatively, a mixture of sweet steviol glycoside compounds may be prepared in solution or suspension and co-dried to produce a powder.

Rebaudioside A is a commercially available material that is typically characterized as being, for example, >80% rebaudioside A, >95% rebaudioside A, or ≥97% of rebaudioside A. Such a purified form of rebaudioside A is typically achieved by reducing the amounts of other steviol glycosides by using solvent recrystallization, adsorption resins, or chromatographic fractionation.

Rebaudioside B may be obtained according to a variety of means. For example, rebaudioside B may recovered from process streams associated with processing and purifying rebaudioside A by using, for example, precipitation, recrystallization, chromatographic fractionation, adsorption resins. Additionally, rebaudioside B may be obtained by the alkaline or acid hydrolysis of rebaudioside A such as disclosed by Kohda, et. al., Phytochemistry, vol. 15, pp. 981-983 (1975) and JP52083731A. Rebaudioside B may also be produced by the enzymatic hydrolysis of rebaudioside A such as disclosed by Mizukani, H., et al., Phytochem vol. 21, pp. 1927-1930 (1982).

Because rebaudioside B may be formed from rebaudioside A, Stevia extracts may have their rebaudioside B content increased by, for example, modifying the process parameters associated with the extraction of steviol glycosides from the Stevia plant. For example, the amount of rebaudioside B may be increased by controlling the pH of a process strewn, the temperature of a process stream, increasing process duration, or a combination of such modifications.

If desired, rebaudioside B may be separated from other steviol glycosides and related compounds using any appropriate method. For example, rebaudioside B may be precipitated from solutions by decreasing the solution pH. Rebaudioside B is typically transformed into its essentially insoluble, protonated form in room temperature water at pH values lower than about 4.5.

After the precipitation of rebaudioside B, it may be separated from the solution comprising solute compounds by any of common means of purifying a suspension. The precipitate can be centrifuged and the supernatant removed. The precipitate can be separated by filtration such as vacuum filtration or the use of a filter press. The soluble and insoluble phases can be separated by use of membranes. The filter cake, centrifuge pellet, or membrane retentate can be further purified by washing with water. Alternatively, the partially purified and recovered precipitate can be re-dissolved in water of pH greater than about 7.7, re-precipitated by the addition of acid to drop pH below about 4.5, and again separated from the impurity-containing liquid phase by any of the above techniques.

Alternatively, rebaudioside B may be precipitated by the addition of a solvent in which rebaudioside B has limited solubility or is insoluble. The specific solvent, amount added, and temperature are preferably to be selected such that essentially only rebaudioside B precipitates, not other compounds.

At neutral pH in water, soluble rebaudioside B may be separated from other soluble compounds by chromatographic fractionation, recrystallization, membrane separation using a membrane of appropriate pore size that retains rebaudiosides but allows smaller molecules to pass, or treatment with adsorptive resins that will either adsorb all impurities, eluting rebaudiosides, or adsorb rebaudiosides and elute all impurities. The resin would then be washed with an eluent having affinity for the adsorbed material, to regenerate the resin (in the first case) or recover the rebaudiosides (second case).

Separated rebaudioside B may be dried by any appropriate method and associated apparatus such as by belt drying, drum drying, tray drying, spray drying, freeze drying, flash drying, or drying with a fluidized bed. Alternatively, instead of drying rebaudioside B and then blending the dried rebaudioside B with rebaudioside A and/or other sweet stevioside compounds, one may blend the same while in solution and then dry the composition.

EXAMPLES

The following disclosed embodiments are merely representative of the invention which may be embodied in various forms. Thus, specific structural, functional, and procedural details disclosed in the following examples are not to be interpreted as limiting.

Example 1—Preference Testing of Commercial
Mixtures of Steviol Glycosides and Rebaudioside B
Enriched Glycoside Mixtures A commercial blend of a steviol glycosides was dissolved in 0.0056 M citric acid buffer pH 3.1. A solution containing a commercially available sweetening composition containing 97% rebaudioside A was similarly prepared.

TABLE 1

| 97% Rebaudioside A and Commercial Blend Compositions. | | |
|---|---|---|
| Glycoside | 97% rebaudioside A, mg | Commercial blend, mg/l |
| Rebaudioside A | 473 | 437 |
| Stevioside | 1 | 35 |
| Rebaudioside B | 14 | 17 |
| Rebaudioside C | 0 | 9 |
| Rebaudioside D | 0 | 20 |
| Total | 498 | 518 |

Thirty-one Tate & Lyle employees participated in paired comparison tests for sweetness and preference. The products were made up in pH 3.1 citric acid buffer (0.9 grams anhydrous citric acid (Tate & Lyle, Decatur, IL) and 026 grams sodium citrate dihydrate (Tate & Lyle, Decatur, IL) per liter and tested at room temperature in two ounce soufflé cups label with random three-digit codes. The presentation order was rotated. The panelists were asked to identify the solution that was sweeter and which they like better. The ballot was presented and the data was collected with SIMS sensory software (Sensory Computer Systems, LLC, Morristown, NJ). Bottled water, a 2% sucrose solution, and unsalted crackers were available for the panelists to clear their palates before and during testing.

The results of the sweetness and preference questions were analyzed with the binomial test and the Thurstonian d' calculated. The p-value for a one-tailed binomial test is calculated as $$1 - \sum_{k=0}^{c} \binom{n}{k} p_0^k (1 - p_0)^{n-k}$$

where c is the number of successes, n is the number of trials, and $p_0$ is the chance probability. A test is considered statistically significant when the p-value is less than the a priori set alpha risk. The two-tailed p-value is double the one-tailed p-value as calculated above.

Thurstonian d' is a linear measure of psychophysical difference. A d' of 1 is generally considered to be a just-noticeable-difference (JND) where a stimulus will be judge stronger in 75% of the trials. The Thurstonian d' is independent of test method and for paired comparison tests is calculated as $$p_c = \Phi(d'/\sqrt{2})$$

where $p_c$ is the proportion of successes, and $\Phi(\bullet)$ is the cumulative distribution function of the standard normal distribution. These statistical terms are more fully defined in standard textbooks on the subject such as "Sensory Discrimination Tests and Measurements", Jian Bi (Blackwell Publishing, 2006).

The instructions for the paired comparison test were:
(i) It is important that you rinse before and between samples.
(ii) Clear your palate with a bite of cracker. Then rinse with the sugar water. Finally rinse with plain water.
(iii) Taste the samples in the order presented, from left to right.

(iv) Taste at least half of the first sample and note the sweetness.
(v) Rinse with the sugar water followed by rinsing with plain water.
(vi) Now taste at least half of the second sample.
(vii) Do not re-taste the first sample.
(viii) Evaluate the samples for preference and sweetness. Pick the sample that you like more and pick the sample that is sweeter. They may or may not be the same sample. If you are not sure or don't have a preference then pick either one.

The questions for the paired comparison test were:
(i) Which of these two samples do you like more?,
(ii) Which of the two samples is sweeter?

The results of this test and the psychophysical d' value are shown in Table 2 below.

TABLE 2

| Commercial Blend vs. 97% rebaudioside A | | |
|---|---|---|
| Sample | # preferring | # sweeter |
| Commercial Blend | 11 | 16 |
| 97% rebaudioside A | 20 | 15 |
| Totals | 31 | 31 |
| Binomial p-value, two tailed | 0.07 | 0.72 |
| d' value | −0.53 | 0.16 |

The results show that the commercial blend was found to be slightly less preferred and about as sweet as the 97% rebaudioside A.

In a subsequent test performed the same way, an addition of rebaudioside B was made to the foregoing Commercial Blend to make a mixture of glycosides that is an embodiment of the present invention having a concentration of rebaudioside B relative to the total amount of sweet steviol glycosides of about 21% and a ratio of rebaudioside A to rebaudioside B of about 3:1.

The glycoside blend of a steviol glycosides was dissolved in 0.0056 M citric acid buffer pH 3.1. A solution containing a commercially available sweetening composition containing 97% rebaudioside A was similarly prepared.

TABLE 3

| 97% rebaudioside A and Glycoside Mixture Compositions. | | |
|---|---|---|
| Glycoside | 97% rebaudioside A, mg | Mixture, mg/l |
| Rebaudioside A | 473 | 350 |
| Stevioside | 1 | 32 |
| Rebaudioside B | 14 | 104 |
| Rebaudioside C | 0 | 10 |
| Rebaudioside D | 0 | 0 |
| Total | 498 | 496 |

The two solutions were presented to a panel of Tate & Lyle employees and they were asked to identify the solution that was sweeter and which they like better using the same instructions and questions as set forth above. The results of the sweetness and preference questions were analyzed with the binomial test and the Thurstonian d' calculated as set forth above. The results and the psychophysical d' value are presented in Table 4 below.

TABLE 4

| Rebaudioside B blend vs. 97% Rebaudioside A | | |
| --- | --- | --- |
| Sample | # preferring | # sweeter |
| Rebaudioside B blend | 27 | 27 |
| 97% rebaudioside A | 11 | 11 |
| Totals | 38 | 38 |
| Binomial p-value, two tailed | <0.01 | <0.01 |
| d' value | 0.79 | 0.79 |

The rebaudioside B blend was both preferred and found to be sweeter than 97% rebaudioside A.

Example 2—Preference Testing of 800 ppm Mixtures of Rebaudioside A or B Mixed with Stevioside A taste panel was asked to compare a commercial mixture of rebaudioside A and stevioside to a 500 ppm sample of 97% rebaudioside A. The glycoside blend of steviol glycosides was dissolved in 0.0056 M citric acid buffer pH 3.1. A solution containing a commercially available sweetening composition containing 97% rebaudioside A was similarly prepared. Sample presentation was rotated and the samples of the two solutions (at room temperature) were presented to a panel of Tate & Lyle employees and they were asked to identify the solution that was sweeter and which they like better using the same instructions and questions as in Example 1. The results of the sweetness and preference questions were analyzed with the binomial test and the Thurstonian d' calculated as in Example 1.

TABLE 5

| 97% Rebaudioside A and Rebaudioside A and Stevioside Mixture Compositions. | | |
| --- | --- | --- |
| Glycoside | 97% rebaudioside A, mg | Mixture, mg/l |
| Rebaudioside A | 473 | 374 |
| Stevioside | 1 | 403 |
| Rebaudioside B | 14 | 11 |
| Rebaudioside C | 0 | 0 |
| Rebaudioside D | 0 | 0 |
| Total | 498 | 789 |

Another panel was asked to compare a mixture of rebaudioside B and Stevioside. The glycoside blend of steviol glycosides was dissolved in 0.0056 M citric acid buffer pH 3.1. A solution containing a commercially available sweetening composition containing 97% rebaudioside A was similarly prepared. The two solutions were presented to a panel of Tate & Lyle employees and they were asked to identify the solution that was sweeter and which they like better using the same instructions and questions as in Example 1.

TABLE 6

| 97% Rebaudioside A and Rebaudioside B and Stevioside Mixture Compositions. | | |
| --- | --- | --- |
| Glycoside | 97% rebaudioside A, mg | Mixture, mg/l |
| Rebaudioside A | 473 | 4 |
| Stevioside | 1 | 397 |

TABLE 6-continued

| 97% Rebaudioside A and Rebaudioside B and Stevioside Mixture Compositions. | | |
| --- | --- | --- |
| Glycoside | 97% rebaudioside A, mg | Mixture, mg/l |
| Rebaudioside B | 14 | 400 |
| Rebaudioside C | 0 | 0 |
| Rebaudioside D | 0 | 0 |
| Total | 498 | 801 |

The results of the sweetness and preference questions were analyzed with the binomial test and the Thurstonian d' calculated as in Example 1. The results of the two panels and the psychophysical d' values are shown in Table 7 and Table 8 respectively.

TABLE 7

| Rebaudioside A & stevioside blend vs. 97% Rebaudioside A | | |
| --- | --- | --- |
| Sample | # preferring | # sweeter |
| Rebaudioside A and stevioside | 4 | 22 |
| 97% rebaudioside A | 37 | 19 |
| Totals | 41 | 41 |
| Binomial p-value, two tailed | <0.01 | 0.27 |
| d' value | −1.83 | 0.13 |

The results show that the rebaudioside A-stevioside blend was much less preferred as compared to 97% rebaudioside A and was found to be nearly equally sweet.

TABLE 8

| Rebaudioside B & stevioside blend vs. 97% Rebaudioside A | | |
| --- | --- | --- |
| Sample | # preferring | # sweeter |
| rebaudioside B and stevioside | 21 | 30 |
| 97% rebaudioside A | 22 | 13 |
| Binomial p-value, two tailed | 0.38 | <0.01 |
| Totals | 43 | 43 |
| d' value | −0.04 | 0.73 |

The results show that the rebaudioside B-stevioside blend was equally preferred to the 97% rebaudioside A (500 ppm) and the rebaudioside B-stevioside blend found to be sweeter than the 97% rebaudioside A.

Example 3—Preference Testing Mixtures of Rebaudioside A or B

A taste panel was asked to compare a commercial mixture of rebaudioside A and rebaudioside B and a 900 ppm sample of 97% rebaudioside A. Tate &Lyle employees participated in paired comparison tests for sweetness and preference. Samples were tested at room temperature in two ounce soufflé cups label with random three-digit code& The presentation order was not rotated because of carryover of the off-flavor of rebaudioside A at 900 ppm. The panelist evaluated the test sample first and then the control 900 ppm rebaudioside A sample. The panelists were instructed not to re-taste the samples. Additionally, the panelists were required to wait one minute between testing samples and instructed to clear their palates with a 2% sucrose solution, an unsalted cracker, and bottled water. The panelists were asked to identify the solution that was sweeter and which they like better. The ballot was presented and the data was collected with SIMS sensory software (Sensory Computer Systems, LLC, Morristown, NJ).

TABLE 9

97% Rebaudioside A and Rebaudioside A and Rebaudioside B Mixture Compositions.

| Ingredient | Test | Control |
|---|---|---|
| Hinkley Spring Water | 98.88 | 98.88 |
| Rebaudioside A | 0.0536 | 0.0900 |
| Rebaudioside B | 0.0310 | 0.0000 |
| Phosphoric Acid, 85% | 0.0361 | 0.0361 |
| Total | 100 | 100 |

The instructions for the paired comparison test were:
(i) It is important that you rinse before and between samples.
(ii) Clear your palate with a bite of cracker. Then rinse with the sugar water. Finally rinse with plain water.
(iii) Taste the samples in the order presented, from left to right.
(iv) Taste at least half of each sample and note the sweetness.
(v) Rinse with the sugar water followed by rinsing with plain water.
(vi) Evaluate the samples for preference and sweetness. Pick the sample that you like more and pick the sample that is sweeter. They may or may not be the same sample. If you are not sure or don't have a preference then pick either one.
(vii) Taste the sample on the left now.
(viii) Wait one minute before tasting the next sample (60 second timer started in SIMS)
(ix) Taste the sample on the right now.
The questions for the paired comparison test were:
(i) Which of these two samples do you like more? Carefully check the 3-digit code before marking your answer. They may not appear in the same order as the samples were presented.
(ii) Which of the two samples is sweeter?
(120 second timer started in SIMS between tests). The results of the sweetness and preference questions were analyzed with the binomial test and the Thurstonian d' calculated as in Example 1.

The results of the two panels and the psychophysical d' values are shown in Table 11.

TABLE 11

Rebaudioside A & Rebaudioside B vs. 97% Rebaudioside A

| | sweetness | p-value two-tailed | d' | preference | p-value one-tailed | d' |
|---|---|---|---|---|---|---|
| Test 1 536 ppm Reb A 310 ppm Reb B | 23 | 0.14 | 0.38 | 36 | <0.01 | 2.29 |
| control 900 ppm Reb A | 15 | | | 2 | | |

The results show that the rebaudioside A-Rebaudioside B blend was preferred as compared to 97% rebaudioside A and was found to be nearly equally sweet.

Example 4—Preference Testing of Mixtures of Steviol Glycosides

This study was performed to determine the preference for blends of rebaudioside A and rebaudioside B relative to rebaudioside A alone at a sweetness of approximately 10 SEV with the sensory methodology changed to reduce panelist confusion with the ballot and requiring the panelist testers to consume approximately 2 ounces of each sample.

Panelists were used in paired comparison tests for sweetness and preference. The products were tested at refrigerated temperature in two ounce soufflé cups label with three-digit codes. The samples were poured immediately before serving. The panelists were asked to identify the beverage that is sweeter and which they like better. Bottled water, a 2% sucrose solution, and unsalted crackers were available for the panelists to clear their palates before and during testing.

The panelists evaluated the test sample first and then evaluated the control 900 ppm rebaudioside A sample second. The presentation order in this test was not rotated because of carryover of the off-flavor of rebaudioside A at 900 ppm. The panelists were instructed to consume all of the samples and not to re-taste the samples. The panelists were alerted to the fact that the order of the samples on the ballot may not be the same as the order the samples are presented. The panelists were instructed to mark the sample they prefer with an adhesive-backed note and these results were compared to the results from the ballot. There was an enforced rest of one minute between samples and two minutes between tests where the panelists were instructed to clear their palates with 2% sucrose, cracker, and water.

The products tested were lemon-lime carbonated soft drinks comprising one part syrup and four parts carbonated water, wherein the syrups had the compositions set forth in Table 12, below.

TABLE 12

Syrup Formulations

| Ingredient | Test 1 | Control |
|---|---|---|
| Hinkley Spring Water | 98.20 | 98.18 |
| Sodium Benzoate | 0.10 | 0.10 |
| REB A | 0.268 | 0.450 |
| REB B | 0.155 | 0.000 |
| Sodium Citrate Dihydrate | 0.15 | 0.15 |
| Citric Acid Anhydrous | 0.63 | 0.63 |
| Givaudan Natural Lemon Flavor #881337 | 0.50 | 0.50 |
| Total | 100 | 100 |

The results were analyzed with the binomial test at an alpha risk of 0.05 as a one-tailed test for preference and two-tailed test for sweetness. The results of the test are set forth in Table 13, below.

TABLE 13

| | | | | | | |
|---|---|---|---|---|---|---|
| Test 1 Beverage compared Control Beverage | | | | | | |
| | sweetness | p-value two-tailed | d' | preference | p-value one-tailed | d' |
| Test 1 536 ppm RebA 310 ppm Reb B | 20 | 0.76 | −0.04 | 26 | 0.03 | 0.48 |
| control 900 ppm RebA | 21 | | | 15 | | |

The tests show that both of the test lemon-lime carbonated soft drinks did not significantly different in sweetness from the rebaudioside A sweetened lemon-lime carbonated soft drink and that they were significantly preferred to the rebaudioside A sweetened lemon-lime carbonated soft drink.

The analysis suggests that a blend of rebaudioside A and rebaudioside B should be more pleasant than rebaudioside A alone especially at higher sweetness levels.

Example 5—Solubility

To determine the solubility of rebaudioside A and rebaudioside B in certain solutions, four stock solutions were prepared. A 10× concentrated citric acid/sodium citrate pH 3 stock buffer solution was prepared by dissolving 0.9 g anhydrous citric acid and 0.26 g of sodium citrate dihydrate in water to make 100 mL of buffer (0.047 M citric acid+ 0.0088 M sodium citrate). A 2500 ppm (nominal) solution of rebaudioside A was prepared by dissolving 0.125 g of GLG RA 97 to make 50 mL of solution. A 2500 ppm (nominal) solution of stevioside was prepared by dissolving 0.125 g of GLG STV 97 to make 50 mL of solution. A 1000 ppm (nominal) solution of rebaudioside B was prepared by diluting 56 mL of a solution assayed at 1790 ppm to make 100 mL of solution.

These solutions were mixed as 1 mL total amounts by micropipetting the volumes, in microliters, into 1.5 mL microcentrifuge tubes As shown in Table 14. The resulting nominal concentrations of each of the three glycosides, in ppm, are also listed in Table 14.

TABLE 14

| | | | | | | | | |
|---|---|---|---|---|---|---|---|---|
| Summary of Test Solutions | | | | | | | | |
| | Microliters of stock solution added | | | | | | | |
| | 10X | | 2500 ppm | 2500 ppm | 1000 ppm | PPM (nominal) | | |
| Tube | citric acid | Water | Reb A | stevioside | Reb B | Reb A | stevioside | Reb B |
| 1 | 100 | 200 | 0 | 200 | 500 | 0 | 500 | 500 |
| 2 | 100 | 250 | 0 | 150 | 500 | 0 | 375 | 500 |
| 3 | 100 | 300 | 0 | 100 | 500 | 0 | 250 | 500 |
| 4 | 100 | 350 | 0 | 50 | 500 | 0 | 125 | 500 |
| 5 | 100 | 400 | 0 | 0 | 500 | 0 | 0 | 500 |
| 6 | 100 | 150 | 50 | 200 | 500 | 125 | 500 | 500 |
| 7 | 100 | 200 | 50 | 150 | 500 | 125 | 375 | 500 |
| 8 | 100 | 250 | 50 | 100 | 500 | 125 | 250 | 500 |
| 9 | 100 | 300 | 50 | 50 | 500 | 125 | 125 | 500 |
| 10 | 100 | 350 | 50 | 0 | 500 | 125 | 0 | 500 |
| 11 | 100 | 100 | 100 | 200 | 500 | 250 | 500 | 500 |
| 12 | 100 | 150 | 100 | 150 | 500 | 250 | 375 | 500 |
| 13 | 100 | 200 | 100 | 100 | 500 | 250 | 250 | 500 |
| 14 | 100 | 250 | 100 | 50 | 500 | 250 | 125 | 500 |
| 15 | 100 | 300 | 100 | 0 | 500 | 250 | 0 | 500 |
| 16 | 100 | 50 | 150 | 200 | 500 | 375 | 500 | 500 |
| 17 | 100 | 100 | 150 | 150 | 500 | 375 | 375 | 500 |
| 18 | 100 | 150 | 150 | 100 | 500 | 375 | 250 | 500 |
| 19 | 100 | 200 | 150 | 50 | 500 | 375 | 125 | 500 |
| 20 | 100 | 250 | 150 | 0 | 500 | 375 | 0 | 500 |
| 21 | 100 | 0 | 200 | 200 | 500 | 500 | 500 | 500 |
| 22 | 100 | 50 | 200 | 150 | 500 | 500 | 375 | 500 |
| 23 | 100 | 100 | 200 | 100 | 500 | 500 | 250 | 500 |
| 24 | 100 | 150 | 200 | 50 | 500 | 500 | 125 | 500 |
| 25 | 100 | 200 | 200 | 0 | 500 | 500 | 0 | 500 |

Immediately after mixing, all of the solutions were clear (vs. cloudy) and showed no precipitation. The tubes were then allowed to stand undisturbed at room temperature in the lab (~25° C.) for around 100 hours, by which time all of them showed at least some precipitation. After standing for five days (~100 hours), the tubes were spun in a bench top microcentrifuge to pelletize the precipitate. The clear supernate was sampled into vials and assayed for glycosides using a reverse phase high performance liquid chromatograph (HPLC) gradient method with UV detection (Waters 2695 Separations Module equipped with a Waters 2487 Dual X Absorbance Detector or equivalent instrumentation) that is summarized in Table 15. The HPLC conditions were as follows:

| | |
|---|---|
| column - | Waters Atlantis T3 4.6 x 250 mm; 4μ with a Phenomenex Security Guard AQ C18 guard cartridge, 4 x 3.0 mm; |
| buffer - | 0.0284% ammonium acetate; 0.0116% acetic acid; |
| flow rate - | 1.0 mL/min; |
| detector - | UV Detector with analysis at 203 nm; |
| inj. vol. - | 20 μL or as desired to conform to standard concentration; and |
| col. temp. - | 40 °C |

TABLE 15

| HPLC Gradient Method: Mobile Phase: Acetonitile/Buffer gradient | | | |
|---|---|---|---|
| Time (min) | % Water | % Buffer | Waters Curve |
| 0 | 70 | 30 | na |
| 15 | 65 | 35 | 6 |
| 20 | 65 | 35 | 6 |
| 25 | 20 | 80 | 6 |
| 30 | 20 | 80 | 1 |
| 35 | 70 | 30 | 1 |

The supernatant data collected from the HPLC were processed using DESIGN EXPERT 8 software. Briefly, the data were entered into the program as "factor" data as a 2 factor-5 level general factorial design as the nominal data which were then converted to numerical data and replaced by the actual HPLC results. The software then selected a model that predicted the concentration (solubility) of rebaudioside B as a function of the concentration of rebaudioside A and stevioside in the supernatant. The software also calculated a number of statistical factors that indicated the significance of the model parameters. In this case, the modeling indicated that models with and without a small rebaudioside A-stevioside interaction parameter were about equally valid so we selected the simpler (non-interacting) model for further processing. The analysis of variance (ANOVA) for this model obtained from the program is shown in Table 16.

TABLE 16

| ANOVA Results-Design Expert | | | | | |
|---|---|---|---|---|---|
| Reb B ANOVA for Response Surface Linear Model Analysis of variance table [Partial sum of squares-Type III] | | | | | |
| Response I Source | Sum of Squares | df | Mean Square | F Value | p-value Prob > F |
| Model | 61253.89 | 2 | 30626.95 | 443.84 | <0.0001 |
| A-Reb A | 61056.01 | 1 | 61056.01 | 884.81 | <0.0001 |
| B-Sievioside | 363.55 | 1 | 363.55 | 5.27 | 0.0316 |
| Residual | 1518.11 | 22 | 69.00 | | |
| Cor total | 62772.00 | 24 | | | |
| Std. Dev. | 8.31 | | R-Squared | 0.9758 | |
| Mean | 301.80 | | Adj R-Squared | 0.9736 | |
| C.V. % | 2.75 | | Pred R-Squared | 0.9691 | |
| PRESS | 1939.25 | | Adeq Precision | 52.665 | |

TABLE 16-continued

ANOVA Results-Design Expert

Reb B
ANOVA for Response Surface Linear Model
Analysis of variance table [Partial sum of squares-Type III]

| Factor | Coefficient Estimate | df | Standard Error | 95% CI Low | 95% CI High | VIF |
|--------|---------------------|----|---------------|-----------|------------|-----|
| Intercept | 297.61 | 1 | 1.67 | 294.15 | 301.08 | |
| A-Reb A | 78.09 | 1 | 2.63 | 72.65 | 83.54 | 1.00 |
| B-Stevioside | −5.66 | 1 | 2.47 | −10.78 | −0.55 | 1.00 |

Final Equation in Terms of Coded Factors:
Reb B=
+297.61
+78.09 *A
−5.66 *B
Final Equation in Terms of Actual Factors:
Reb B=
+225.17918
+0.31238*Reb A
−0.02264 *Stevioside Table 17 shows the experimentally determined compositions of the supernatants from each of the test solutions.

TABLE 17

Raw Assay Data from the HPLC
Assayed glycoside concentrations by HPLC ppm

| Tube | Reb A | stevioside | Reb B | steviolbioside |
|------|-------|-----------|-------|----------------|
| 1 | 38.8 | 478 | 234 | 4.39 |
| 2 | 38.5 | 351 | 231 | 3.61 |
| 3 | 37.6 | 241 | 229 | 2.28 |
| 4 | 36.2 | 112 | 233 | 1.59 |
| 5 | 34.9 | 0 | 226 | 0.73 |
| 6 | 154 | 480 | 265 | 5.03 |
| 7 | 154 | 360 | 255 | 3.35 |
| 8 | 151 | 241 | 284 | 2.86 |
| 9 | 149 | 121 | 273 | 2.03 |
| 10 | 146 | 0 | 271 | 0.77 |
| 11 | 274 | 476 | 300 | 5.1 |
| 12 | 273 | 363 | 293 | 4.51 |
| 13 | 269 | 248 | 305 | 3.38 |
| 14 | 260 | 119 | 286 | 1.49 |
| 15 | 260 | 0 | 308 | 0 |
| 16 | 375 | 473 | 336 | 4.87 |
| 17 | 381 | 357 | 344 | 3.78 |
| 18 | 372 | 245 | 340 | 2.61 |
| 19 | 370 | 125 | 342 | 2 |
| 20 | 365 | 0 | 342 | 0 |
| 21 | 487 | 475 | 361 | 4.74 |
| 22 | 477 | 356 | 363 | 4.35 |
| 23 | 481 | 245 | 358 | 2.72 |
| 24 | 498 | 120 | 375 | 1.25 |
| 25 | 484 | 0 | 391 | 0 |

The rebaudioside B used in this study contained about 6-7% rebaudioside A which explains the rebaudioside A found in tubes 1-5. It is also evident from the data that the concentrations of stevioside and rebaudioside A in the samples are consistent with the belief that these compounds are completely soluble in this buffer at this concentration, i.e., only the rebaudioside B was precipitating in the experiment. The data shown in Table 17 were entered into DESIGN EXPERT 8 and a two factor linear regression model was generated, which is set forth in Equation 1, below.

$$ConcB = 225.18 + 0.312*concA - 0.02264*concSs \quad \text{(Eq. 1)}$$

The equation shows that the concentration of B in the supernatant (concB, i.e., the solubility limit) was found to be influenced by both the concentration of rebaudioside A (concA) and the concentration of stevioside (concSs). The rebaudioside B solubility was increased substantially by increases in the concentration of rebaudioside A, and slightly decreased by the increases in the concentration of stevioside.

The linear-linear model represented by Equation 1 plots as a plane in a 3-D plot as shown in FIG. 1. The plane represents the maximum solubility of rebaudioside B in citric acid buffer (pH 3.1), ranging from a low of about 225 ppm when in 478 ppm stevioside (according to the model) to about 380 ppm in 480 ppm rebaudioside A.

Using the solubility limit (Equation 1) and the constraint that the sum of the mass fractions must add to 1 allows one to find an equation that relates the mass fraction of rebaudioside B ($X_B$) at the solubility limit to the mass fraction of rebaudioside A ($X_A$), the total rebaudioside concentration (rebaudioside B+rebaudioside A+stevioside=$C_{tot}$), and the coefficients ($\alpha_0$=225.18 ppm, $\alpha_1$=0.312, $\alpha_2$=0.0226) of the regression equation (Equation 2, below).

$$X_B = \frac{[\alpha_0/C_{tot} + \alpha_2]}{(1 + \alpha_2)} + \left[\frac{\alpha_1 - \alpha_2}{1 + \alpha_2}\right] X_A \quad \text{(eq. 2)}$$

It is believe that Equation 2, therefore, defines the edge of the stable solution solubility region in ternary mixtures of rebaudioside A, stevioside, and rebaudioside B. Thus, the size of the stable region able region will depend on the total concentration ($C_{tot}$).

This study clearly shows that the solubility of rebaudioside B is limited in pH 3 citric buffer, even though rebaudioside B has high solubility in neutral pH solutions. In addition the presence of rebaudioside A increases the solubility of rebaudioside B, but the presence of stevioside slightly reduces the solubility of rebaudioside B. This solubility information should be noted when attempting to formulate solutions of rebaudioside B and mixtures of rebaudiosides.

Example 6—Evaluation of Sweetener Taste as a Function of Rebaudioside B Content A descriptive panel was used to quantify flavor attributes and intensities of varying levels of rebaudioside B added to rebaudioside A (which was 97% pure and contained 0.62% rebaudioside B). Specifically, the sweeteners were evaluated by the panelists at 900 ppm rebaudioside A+rebaudioside B solutions, wherein the amount of added rebaudioside B was such that the total content of rebaudioside B was 0.6%, 3.6%, 6.5%, 11.4%, 22.3%, 37.5%, and 52%. An 8% sucrose solution as a control. The solutions were prepared in neutral pH water. Other high intensity sweeteners included in the testing were Aspartame at 500 ppm, ASK at 750 ppm, Sucralose at 250 ppm, and *Stevia* at 500 ppm.

Before conducting the testing the ten panelists were extensively trained in the use of standardized vocabulary to describe the appearance, aroma, flavor, and texture of a wide variety of products in order to rate the samples for sweetness, bitterness, off flavor, chemical or artificial sweetener flavor, anise, and mouth coating. Each such attribute was evaluated on a first and second sip, and on after-taste. The testing began with a session to orient the panelists during which they tasted the samples and discussed the flavor characteristics. They also tasted and discussed references for "sweet", "bitter", and "anise". The definitions of flavor terms are set forth in Table 18 below.

TABLE 18

Definitions

| Term | Definition |
| --- | --- |
| Total Flavor | The total intensity of all the aromas or flavors in the product. |
| Sweet | One of tire four basic tastes, perceived primarily on the tip of the tongue; common to sucrose and other sugars. |
| Total Off Flavor | All of the flavors of the sample that are not sweet and would be considered unintended in the sample. |
| Artificial Sweetener/ Chemical | The flavor reminiscent of artificial sweeteners or chemical tastes not intended to be in foods and beverages in the sample. |
| True Bitter | One of the four basic tastes, perceived primarily on the back of the tongue; common to caffeine and quinine, |
| Anise | The total flavor reminiscent of anise or licorice. |
| Mouthcoating | The feeling of any type of coating on the soft tissues of the mouth. |

During the second and third days of testing, the panelists evaluated the samples for the various attributes and rated them on a scale from none to extreme that encompasses all food ingredient products, not just sweeteners. The products and solutions set forth in Table 19 were used to "anchor" the panelist to the scales.

TABLE 19

Flavor Anchors

| Flavor | Scale Value | Reference |
| --- | --- | --- |
| Anise | NR | Anise on blotter |
| Sweet | 5.0 | 5% Sucrose in Water |
| | 10.0 | 10% Sucrose in Water |
| Bitter | 2.0 | 0.025% Caffeine in Water |
| | 5.0 | 0.04% Caffeine in Water |

Eight samples were evaluated per session. A 7 minute rest break was given between each sample and a 15 minute break was given after the first 4 samples had been evaluated. Two evaluations (i.e. replicates) were obtained from each panelist for each product; therefore, a total of 20 judgments were obtained for each product. During data collection, the panelists were instructed to indicate the intensity of each sensory characteristic by placing a vertical slash on 15-cm line scales. The serving order was balanced, with products seen approximately an equal number of times in each possible position. In the waiting room, ambient Alhambra drinking water, unsalted soda crackers, and celery were provided for cleansing the palate between samples.

Slash marks on the line scales were converted to numbers ranging from 1 to 15 by SIMS, the computerized sensory data collection system. Mean intensities were calculated for each sensory characteristic. Analysis of Variance and Duncan's Multiple Range Test, where appropriate, were used to determine significant differences among the samples for each attribute. When panelist-by-product interactions were significant, the mean square of the interaction term, instead of the mean square of the error term, was used in calculation of the product F values. The results are set forth in Tables 20 and 21, below.

TABLE 20

QUANTITATIVE DESCRIPTIVE EVALUATIONS OF BITTER MASKERS
n = 18 (9 Panelists, 2 Evaluations Each)

| | Sucrose | 0.6% Reb B | 3.6% Reb B | 6.5% Reb B | 11.4% Reb B | 22.3% Reb B | 37.5% Reb B | 52% Reb B | P-Value | Conf. Level |
| --- | --- | --- | --- | --- | --- | --- | --- | --- | --- | --- |
| TOTAL FLAVOR: | | | | | | | | | | |
| First Sip | d 8.67 | abc 9.94 | a 10.15 | ab 10.04 | bc 9.69 | bc 9.61 | abc 9.76 | c 9.47 | 0.0008 | ** |
| Second Sip | c 7.86 | ab 8.62 | a 8.79 | ab 8.56 | bc 8.28 | c 8.07 | c 8.00 | c 7.97 | 0.0047 | ** |
| Aftertaste | d 4.32 | ab 5.96 | a 6.34 | bc 5.77 | bc 5.59 | bc 5.80 | c 5.45 | bc 5.63 | 0.0001 | ** |
| SWEET: | | | | | | | | | | |
| First Sip | d 8.06 | abc 9.15 | ab 9.34 | a 9.56 | abc 9.13 | bc 9.01 | abc 9.21 | c 8.80 | 0.0057 | ** |
| Second Sip | 7.43 | 7.27 | 7.66 | 7.36 | 7.40 | 6.92 | 6.91 | 7.02 | 0.2088 | NSD |
| Aftertaste | c 3.92 | bc 4.44 | a 5.15 | ab 4.70 | ab 4.58 | ab 5.01 | ab 4.61 | ab 4.75 | 0.0184 | ** |

TABLE 20-continued

| QUANTITATIVE DESCRIPTIVE EVALUATIONS OF BITTER MASKERS n = 18 (9 Panelists, 2 Evaluations Each) | | | | | | | | | |
| --- | --- | --- | --- | --- | --- | --- | --- | --- | --- |
| | Sucrose | 0.6% Reb B | 3.6% Reb B | 6.5% Reb B | 11.4% Reb B | 22.3% Reb B | 37.5% Reb B | 52% Reb B | P-Value | Conf. Level |
| TOTAL OFF FLAVOR: | | | | | | | | | | |
| First Sip | e 0.89 | ab 7.69 | a 7.79 | abc 7.34 | cd 6.83 | cd 6.72 | bcd 6.98 | d 6.48 | 0.0001 | ** |
| Second Sip | c 0.49 | a 7.01 | a 7.02 | a 6.88 | b 6.09 | b 5.67 | b 5.83 | b 5.68 | 0.0001 | ** |
| ARTIFICIAL SWEETENER/ CHEMICAL: | | | | | | | | | | |
| First Sip | d 0.59 | a 7.74 | ab 7.45 | ab 7.37 | c 6.67 | c 6.54 | bc 6.87 | c 6.52 | 0.0001 | ** |
| Second Sip | c 0.41 | a 6.79 | a 6.88 | a 6.71 | b 5.73 | b 5.31 | b 5.48 | b 5.64 | 0.0001 | ** |
| Aftertaste | f 0.12 | ab 5.00 | a 5.22 | bc 4.66 | cd 4.39 | de 3.99 | e 3.79 | de 3.91 | 0.0001 | ** |

Analysis of Variance Confidence Levels: * = 90%, ** = 95%
NSD: Not significantly different at confidence levels of 90% or higher.
*Mean ratings with different superscripts differ significantly at the 90% confidence level (Duncan's Multiple Range Test).

TABLE 21

| QUANTITATIVE DESCRIPTIVE EVALUATIONS OF BITTER MASKERS (continued) n = 18 (9 Panelists, 2 Evaluations Each) | | | | | | | | | |
| --- | --- | --- | --- | --- | --- | --- | --- | --- | --- |
| | Sucrose | 0.6% Reb B | 3.6% Reb B | 6.5% Reb B | 11.4% Reb B | 22.3% Rob B | 37.5% Reb B | 52% Reb B | P-Value | Conf. Level |
| TRUE BITTER: | | | | | | | | | | |
| First Sip | e 0.29 | a 3.78 | ab 3.63 | abc 3.28 | ab 3.37 | cd 2.80 | bc 3.11 | d 2.49 | 0.0001 | ** |
| Second Sip | d 0.24 | a 3.89 | ab 3.71 | ab 3.46 | b 3.36 | c 2.81 | c 2.62 | c 2.74 | 0.0001 | ** |
| Aftertaste | e 0.15 | a 3.39 | a 3.45 | b 2.78 | bc 2.57 | bcd 2.26 | cd 2.08 | d 1.89 | 0.0001 | ** |
| ANISE: | | | | | | | | | | |
| First Sip | c 0.52 | ab 1.73 | ab 1.73 | ab 1.45 | a 1.79 | ab 1.59 | ab 1.58 | b 1.34 | 0.0001 | ** |
| Second Sip | b 0.41 | a 1.53 | a 1.64 | a 1.36 | a 1.62 | a 1.34 | a 1.36 | a 1.29 | 0.0001 | ** |
| Aftertaste | d 0.13 | a 1.42 | a 1.46 | abc 1.27 | ab 1.34 | c 0.98 | abc 1.12 | bc 1.03 | 0.0001 | ** |
| MOUTH-COATING: | | | | | | | | | | |
| First Sip | c 0.76 | b 1.47 | b 1.48 | b 1.40 | a 1.74 | b 1.49 | b 1.49 | b 1.37 | 0.0001 | ** |
| Second Sip | b 0.89 | a 1.48 | a 1.46 | a 1.29 | a 1.56 | a 1.42 | a 1.40 | a 1.42 | 0.0001 | ** |

Analysis of Variance Confidence Levels: * = 90%, ** = 9.5%
NSD: Not significantly different at confidence levels of 90% or higher,
Mean ratings with different superscripts differ significantly at the 90% confidence level (Duncan's Multiple Range Test).

Figure 3:
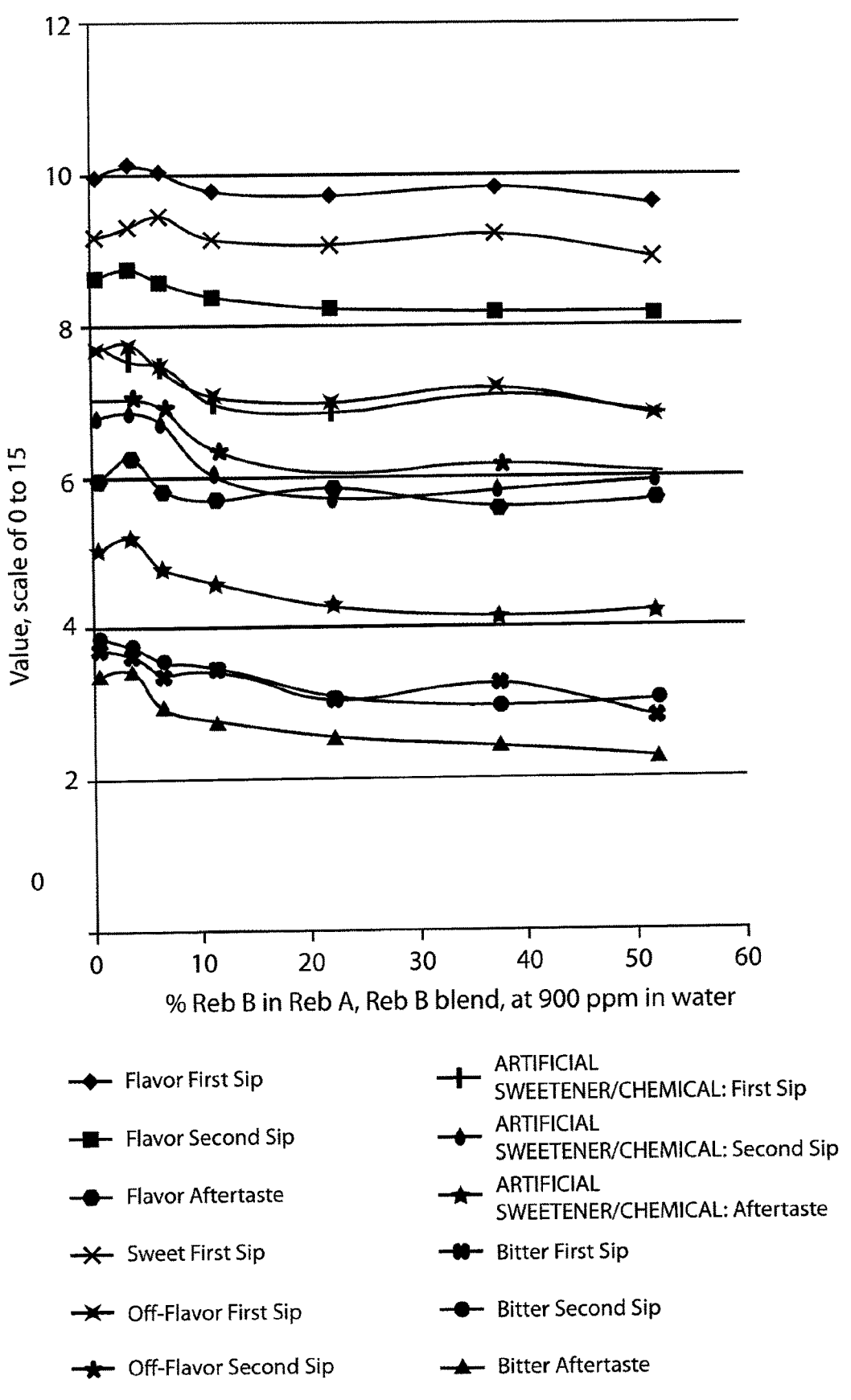
FIG. 3 is a graph showing the effect of rebaudioside B content (in a solution containing rebaudioside A and added rebaudioside B for a total concentration of 900 ppm in water) on various flavor attributes as scored by taste panelists.

FIG. 3 shows the magnitude of the mean responses of the panelists of each flavor attribute for which statistically significant differences were measured as a function of rebaudioside B content. Because the scale used encompasses "the universe", the magnitude of differences between the 97% rebaudioside A solution and increasing levels of rebaudioside B is not as large as other informal testing determined. For example, several informal testers believed that adding about 20% rebaudioside A reduced the bitterness by about 80% whereas the results from above-described panel of tasters showed that adding about 20% rebaudioside A reduced bitterness by about 30%.

The flavor attributes were also compared between the samples. An attribute is mentioned as 'highest' or 'lowest' if the sample's attribute was significantly higher or lower than all of the other samples. An attribute is mentioned as 'high' or 'low' if the sample's attribute was the highest or lowest, respectively, but not significantly higher or lower than all of the other samples. Attributes discussed herein were found to be significant at the 95% confidence level.

Compared to the high intensity sweetener samples, sucrose was the Lowest in the following: Total Flavor (although not significantly on the second sip vs. 22.3%, 37.5%, and 52% rebaudioside B); Sweetness on the first sip and in the aftertaste (although not significantly lower than the bitter control); Total Off Flavor; Artificial Sweetener/Chemical; True Bitter; Anise; and Mouthcoating.

Among the high intensity sweetener samples the 97% rebaudioside with 0.6% rebaudioside B was High in the following: Total Off Flavor on the second sip; Artificial Sweetener/Chemical on the first and second sips; True Bitter; and Anise in the aftertaste.

Among the high intensity sweeteners samples, the sample with 3.6% of rebaudioside B added was High in the following: Total Flavor; Sweetness in the aftertaste; Total Off Flavor; Artificial Sweetener/Chemical on the second sip and in the aftertaste; True Bitter in the aftertaste; and Anise in the aftertaste.

Among the high intensity sweeteners samples, the sample with 6.5% of rebaudioside B added was High in the following: Sweetness in the first sip; Total Off Flavor on the second sip; and Artificial Sweetener/Chemical on the second sip.

Among the high intensity sweeteners samples, the sample with 11.4% of rebaudioside B added was Low in Total Off Flavor on the second sip and Artificial Sweetener/Chemical on the first and second sips and High in Anise on the first sip and Mouthcoating on the first sip.

Among the high intensity sweeteners samples, the sample with 22.3% of rebaudioside B added was Low in the following: Total Flavor on the second sip Total; Total Off Flavor on the second sip; Artificial Sweetener/Chemical on the first and second-sips; True Bitter on the second sip; and Anise in the aftertaste.

Among the high intensity sweeteners samples, the sample with 37.5% of rebaudioside B added was Low in the following: Total Flavor on the second sip and in the aftertaste; Total Off Flavor on the second sip; Artificial Sweetener/Chemical on the second sip and in the aftertaste; and True Bitter on the second sip.

Among the high intensity sweeteners samples, the sample with 52% of rebaudioside B added was Low in the following: Total Flavor on the first and second sips; Sweet on the first sip; Total Off Flavor on the first and sips; Artificial Sweetener/Chemical on the first and second sips; True Bitter; and Anise on the first sip.

The results indicate that the addition of 3.6% of rebaudioside B resulted in worse flavor attributes and the addition of 6.5% of rebaudioside B had little impact on the Total Off Flavor and Artificial Sweetener/Chemical Flavor. The addition of greater amounts of rebaudioside B tended to result in the samples scoring more closely to sucrose in most characteristics with decreasing off flavors, particularly bitterness. That said, the results show that the increases the rebaudioside B content above about 20% had little further impact on undesirable flavor attributes. Surprisingly, the sweetness remained fairly unaffected by the rebaudioside B content, which is contrary to previous reports regarding rebaudioside B that found it to be one-half to two-thirds as sweet as rebaudioside A. Although the Sweetness and Total Flavor of the high intensity sweetener solutions were similar to the 8% sucrose solution, and similar to each other, the Artificial Sweetener/Chemical tastes were much higher than the sucrose solution, with a greater spread among high intensity sweetener samples, which indicates that the rebaudioside B concentration had a significant impact on these tastes.

Advantageously, the present invention may be used to produce high intensity sweetener compositions that can be used to provide the "full" sweetness needed for many applications, which typically cannot be achieved with rebaudioside A alone because of its bitterness at concentrations above about 200 ppm. More specifically, because the present invention allows for the production of high intensity sweeteners that may be added to consumables such that the consumables comprises about 800 to about 1000 ppm of rebaudiosides without the consumable having unacceptable levels of bitterness, sweetener compositions of the present invention may be used to provide the entire sweetness needed for many consumables (food applications).

What is claimed is:

1. A *Stevia* extract comprising rebaudioside B at a concentration that is in the range of 10 to about 90% by weight of the *Stevia* extract.

2. The *Stevia* extract of claim 1, wherein the concentration of rebaudioside B is in the range of about 15 to about 50% by weight of the *Stevia* extract.

3. The *Stevia* extract of claim 1, wherein the concentration of rebaudioside B is in the range of about 15 to about 30% by weight of the *Stevia* extract.

4. The *Stevia* extract of claim 1, wherein the concentration of rebaudioside B is in the range of about 20 to about 25% by weight of the *Stevia* extract.

5. A sweetening composition comprising sweet steviol glycoside compounds, wherein the sweet steviol glycoside compounds comprise rebaudioside B at a concentration that is in the range of 10% to about 90% by weight of the total amount of sweet steviol glycoside compounds in the sweetening composition.

6. The sweetening composition of claim 5, wherein the concentration of the rebaudioside B is in the range of about 15% to about 50% by weight of the total amount of sweet steviol glycoside compounds in the sweetening composition.

7. The sweetening composition of claim 5, wherein the rebaudioside B is at a concentration that is at least about 15% and no greater than about 30% by weight of the total amount of sweet steviol glycoside compounds in the sweetening composition.

8. The sweetening composition of claim 5, wherein the rebaudioside B is at a concentration that is at least about 20% and no greater than about 25% by weight of the total amount of sweet steviol glycoside compounds in the sweetening composition.

9. A consumable comprising a sweetening composition that comprises sweet steviol glycoside compounds, wherein the sweet steviol glycoside compounds comprise rebaudioside B at a concentration that is in the range of 10% to about 90% by weight of the total amount of sweet steviol glycoside compounds in the sweetening composition.

10. The consumable of claim 9, wherein the sweet steviol glycosides are at a total concentration that less than their sweetening threshold.

11. The consumable of claim 9, wherein the sweet steviol glycosides are at a total concentration that is in the range of about 50 ppm to about 2000 ppm and the rebaudioside B is at a total concentration of at least about 20 ppm.

12. The consumable of claim 11, wherein the rebaudioside B is at a total concentration of at least about 50 ppm and no greater than about 500 ppm.

13. The consumable of claim 11, wherein the rebaudioside B is at a total concentration of at least about 100 ppm and no greater than about 400 ppm.

14. The consumable of claim 11, wherein the rebaudioside B is at a total concentration of at least about 200 ppm and no greater than about 300 ppm.

15. The consumable of claim 9, wherein the consumable is selected from the group consisting of a beverage selected from the group consisting of carbonated soft drinks, powdered soft drinks, ready to drink teas, sports drinks, dairy drinks, yogurt-containing drinks, alcoholic beverages, energy drinks, flavored waters, vitamin drinks, fruit drinks, and fruit juices; a foodstuff selected from the group consisting of baked goods, soups, sauces, processed meats canned fruits, canned vegetables, dairy products, frozen confections, confections, chewing gums, cakes, cookies, bars, and other sweet bakery items, cereals, cereal bars, yogurt, energy bars, granola bars, hard candy, jelly candy, chocolate candy, and other sweet confections; an oral care product selected from the group consisting of toothpastes, mouthwashes, and oral rinses; a tobacco product selected from the group consisting of snuff and chewing tobacco; a pharmaceutical selected from the group consisting of tablets, lozenges, and suspensions; a nutraceutical product selected from the group consisting of supplements and vitamins.

16. A method of sweetening a consumable, the method comprising including an effective amount of the sweetening composition in the consumable, wherein the sweetening composition comprises sweet steviol glycoside compounds, wherein the sweet steviol glycoside compounds comprise rebaudioside B at a concentration that is in the range of 10% to about 90% by weight of the total amount of sweet steviol glycoside compounds in the sweetening composition.

* * * * *